(12) United States Patent
Bruce et al.

(10) Patent No.: US 9,656,015 B2
(45) Date of Patent: *May 23, 2017

(54) SELECTIVE CHEMOKINE MODULATION

(71) Applicant: Prophy Med AB, Viken (SE)

(72) Inventors: Lars Bruce, Viken (SE); Staale Petter Lyngstadaas, Nesoddtangen (NO)

(73) Assignee: PROPHY MED AB, Viken (SE)

( * ) Notice: Subject to any disclaimer, the term of this patent is extended or adjusted under 35 U.S.C. 154(b) by 222 days.

This patent is subject to a terminal disclaimer.

(21) Appl. No.: 14/312,557

(22) Filed: Jun. 23, 2014

(65) Prior Publication Data

US 2014/0299548 A1    Oct. 9, 2014

Related U.S. Application Data

(62) Division of application No. 12/441,000, filed as application No. PCT/SE2007/000785 on Sep. 11, 2007, now Pat. No. 8,784,845.

(60) Provisional application No. 60/843,760, filed on Sep. 12, 2006.

(51) Int. Cl.
| | |
|---|---|
| A61K 9/00 | (2006.01) |
| A61M 1/38 | (2006.01) |
| A61K 33/24 | (2006.01) |
| B01J 20/02 | (2006.01) |
| B01J 20/06 | (2006.01) |
| A61M 1/36 | (2006.01) |
| A61K 9/14 | (2006.01) |

(52) U.S. Cl.
CPC ............. *A61M 1/38* (2013.01); *A61K 9/14* (2013.01); *A61K 33/24* (2013.01); *A61M 1/3679* (2013.01); *B01J 20/02* (2013.01); *B01J 20/06* (2013.01)

(58) Field of Classification Search
CPC .. B01J 20/02; B01J 20/06; A61K 9/14; A61K 33/24; A61M 1/38; A61M 1/3679
See application file for complete search history.

(56) References Cited

U.S. PATENT DOCUMENTS

| | | |
|---|---|---|
| 6,527,951 B1 | 3/2003 | Tuvim |
| 2003/0055106 A1 | 3/2003 | Faure et al. |
| 2005/0119105 A1 | 6/2005 | Zimmer et al. |

FOREIGN PATENT DOCUMENTS

| | | | |
|---|---|---|---|
| EP | 0686848 A1 | 12/1995 | |
| GB | 2252729 A | 8/1992 | |
| WO | 01/12180 A2 | 2/2001 | |
| WO | 03/059834 A1 | 7/2003 | |
| WO | 2006/055675 A1 | 5/2006 | |
| WO | WO2006055675 | * 5/2006 | ................. 424/400 |

OTHER PUBLICATIONS

Deng et al (J. Immunol., 1994, 153(5), 2130-2136).*
Spurrell et al, Am. J. Physiol. Lung Cell. Mol. Physiol., 289:L85-L95 (Mar. 2005).
Ingram et al, Respiratory Research, BioMed Central, 8(1):34 (Apr. 25, 2007).
Antao-Menezes et al, Journal of Immunology, 180(6):4200-4207 (Mar. 15, 2008).
European Search Report from corresponding EP 07808800 dated Nov. 13, 2009.
Suzuki et al, Journal of Biomedical Materials Research, Part A, 66A(2):396-402 (2003).
English Translation of Official Action from corresponding JP 2009-528196 dated Nov. 27, 2012.
Tinoco et al, Inorg. Chem., 47:8380-8390 (Sep. 15, 2008, online Aug. 19, 2008).
Dover et al, J. Med. Chem., 54:6157-6165 (2011).
Liu et al, Cytokine & Growth Factor Reviews, 22:121-130 (2011).

* cited by examiner

*Primary Examiner* — Jason Sims
*Assistant Examiner* — Ibrahim D Bori
(74) *Attorney, Agent, or Firm* — Porter Wright Morris & Arthur LLP

(57) ABSTRACT

A body fluid purifying arrangement comprises a purifying chamber having a fluid input and a fluid output, a first filter arranged in connection the fluid input, and a second filter arranged in connection with the fluid output. In another embodiment, a body fluid purifying arrangement in the form of a syringe comprises a purifying chamber having a common fluid input and fluid output, and a filter arranged in connection with the common fluid input and output. Granules or particles made of a metal or an oxide of a metal are retained within the purifying chamber by the respective filter(s) to purify a body fluid passing through the purifying chamber from 10 kDa interferon-γ inducible protein, IP-10, wherein said metal is a metal of group 4 or 5 of the periodic table of the elements and selected from the group consisting of titanium, zirconium, hafnium, niobium and tantalum.

20 Claims, 10 Drawing Sheets

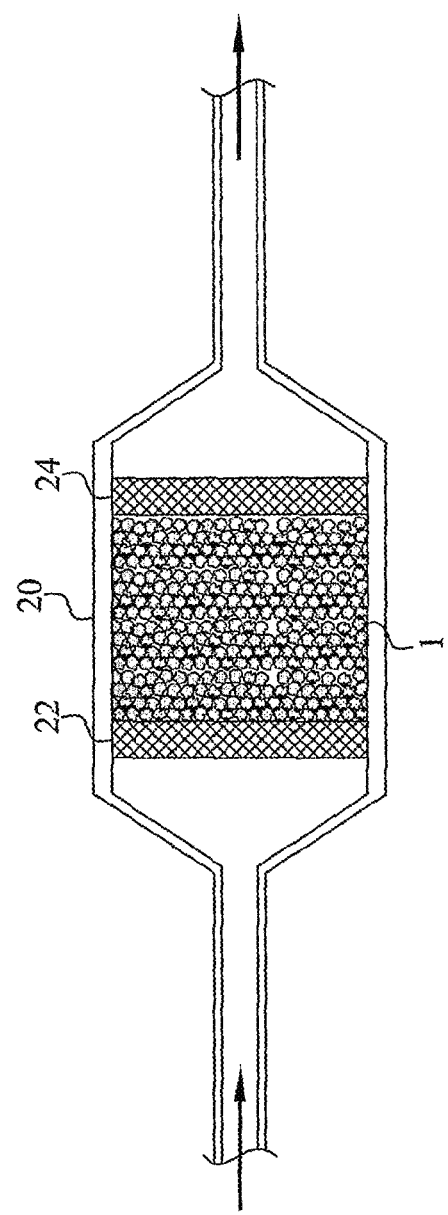
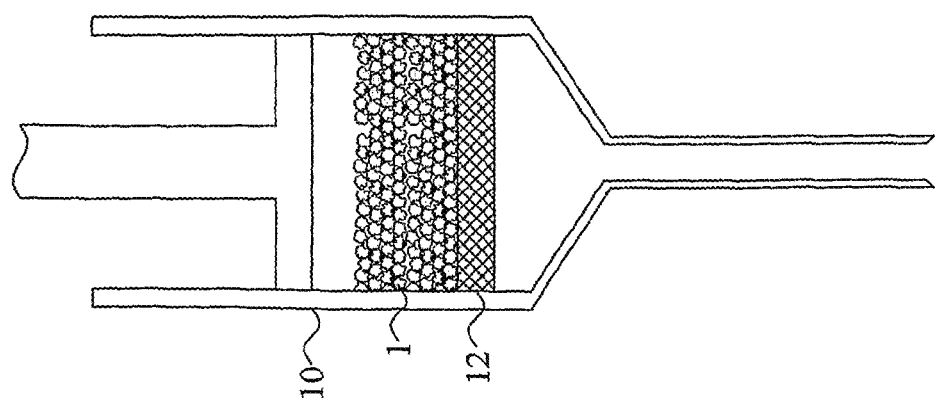

SEQUENCE LISTING

<160> NUMBER OF SEQ ID NOS: 14

<210> SEQ ID NO 1
<211> LENGTH: 23
<212> TYPE: DNA
<213> ORGANISM: Artificial Sequence
<220> FEATURE:
<223> OTHER INFORMATION: Synthetic Sense Primer

<400> SEQUENCE: 1

```
gctacaatga aaaagaaggg tga                                              23

<210> SEQ ID NO 2
<211> LENGTH: 20
<212> TYPE: DNA
<213> ORGANISM: Artificial Sequence
<220> FEATURE:
<223> OTHER INFORMATION: Synthetic Antisense Primer

<400> SEQUENCE: 2
tagggaagtg atgggagagg                                                  20

<210> SEQ ID NO 3
<211> LENGTH: 20
<212> TYPE: DNA
<213> ORGANISM: Artificial Sequence
<220> FEATURE:
<223> OTHER INFORMATION: Synthetic Sense Primer

<400> SEQUENCE: 3
aggagacttg cctggtgaaa                                                  20

<210> SEQ ID NO 4
<211> LENGTH: 19
<212> TYPE: DNA
<213> ORGANISM: Artificial Sequence
<220> FEATURE:
<223> OTHER INFORMATION: Synthetic Antisense Primer

<400> SEQUENCE: 4
gcatttgtgg ttgggtcag                                                   19

<210> SEQ ID NO 5
<211> LENGTH: 21
<212> TYPE: DNA
<213> ORGANISM: Artificial Sequence
<220> FEATURE:
<223> OTHER INFORMATION: Synthetic Sense Primer

<400> SEQUENCE: 5
ttatcttgtc tctgggcttg g                                                21

<210> SEQ ID NO 6
<211> LENGTH: 20
<212> TYPE: DNA
<213> ORGANISM: Artificial Sequence
<220> FEATURE:
<223> OTHER INFORMATION: Synthetic Antisense Primer

<400> SEQUENCE: 6
atgaagtggt tgggaatga                                                   20

<210> SEQ ID NO 7
<211> LENGTH: 20
<212> TYPE: DNA
<213> ORGANISM: Artificial Sequence
<220> FEATURE:
<223> OTHER INFORMATION: Synthetic Sense Primer

<400> SEQUENCE: 7
ctatctggga ggggtcttcc                                                  20

<210> SEQ ID NO 8
<211> LENGTH: 20
<212> TYPE: DNA
```

```
<213> ORGANISM: Artificial Sequence
<220> FEATURE:
<223> OTHER INFORMATION: Synthetic Antisense Primer

<400> SEQUENCE: 8
gggggtaata aagggattgg                                              20

<210> SEQ ID NO 9
<211> LENGTH: 20
<212> TYPE: DNA
<213> ORGANISM: Artificial Sequence
<220> FEATURE:
<223> OTHER INFORMATION: Synthetic Sense Primer

<400> SEQUENCE: 9
ctggaacggt gaaggtgaca                                              20

<210> SEQ ID NO 10
<211> LENGTH: 23
<212> TYPE: DNA
<213> ORGANISM: Artificial Sequence
<220> FEATURE:
<223> OTHER INFORMATION: Synthetic Antisense Primer

<400> SEQUENCE: 10
aagggacttc ctgtaacaat gca                                          23

<210> SEQ ID NO 11
<211> LENGTH: 20
<212> TYPE: DNA
<213> ORGANISM: Artificial Sequence
<220> FEATURE:
<223> OTHER INFORMATION: Synthetic Sense Primer

<400> SEQUENCE: 11
gtaacccgtt gaaccccatt                                              20

<210> SEQ ID NO 12
<211> LENGTH: 20
<212> TYPE: DNA
<213> ORGANISM: Artificial Sequence
<220> FEATURE:
<223> OTHER INFORMATION: Synthetic Antisense Primer

<400> SEQUENCE: 12
ccatccaatc ggtagtagcg                                              20

<210> SEQ ID NO 13
<211> LENGTH: 20
<212> TYPE: DNA
<213> ORGANISM: Artificial Sequence
<220> FEATURE:
<223> OTHER INFORMATION: Synthetic Sense Primer

<400> SEQUENCE: 13
tgcaccacca actgcttagc                                              20

<210> SEQ ID NO 14
<211> LENGTH: 21
<212> TYPE: DNA
<213> ORGANISM: Artificial Sequence
```

-continued

```
<220> FEATURE:
<223> OTHER INFORMATION: Synthetic Antisense Primer

<400> SEQUENCE: 14
ggcatggact gtggtcatga g                                              21
```

SELECTIVE CHEMOKINE MODULATION

SEQUENCE LISTING

The Sequence Listing submitted herewith, entitled 198188-Sequence-Listing.txt, created Jun. 23, 2014 and having a size of 3057 bytes, is incorporated herein by reference.

TECHNICAL FIELD

The present invention generally relates to selective modulation of the chemokine IP-10 and to treating or preventing diseases and pathogenic conditions characterized by adverse IP-10 expression.

BACKGROUND

Cytokines are a group of proteinaceous signaling compounds that are used extensively for inter-cell communication. These compounds are critical to the functioning of both innate and adaptive immune responses. Apart from their importance in the development and functioning of the immune system, cytokines play a major role in a variety of immunological, inflammatory and infectious diseases.

Cytokines are produced by wide variety of cell types (both haemopoietic and non-haemopoietic) and can have effects on both nearby cells or throughout the organism, sometimes strongly dependent on the presence of other chemicals and cytokines.

Each cytokine generally binds to a specific cell-surface receptor. Subsequent cascades of intracellular signaling then alter cell functions. This may include the upregulation and/or downregulation of several genes and their transcription factors, in turn resulting in the production of other cytokines, an increase in the number of surface receptors for other molecules, or the suppression of their own effect by feedback inhibition.

Chemokine refers to a specific class of cytokines that mediate chemoattraction (chemotaxis) between cells. These chemokines are pro-inflammatory activation-inducible cytokines that generally have a molecular mass of between 8 and 10 kDa. Their receptors are mainly integral membrane proteins containing seven membrane-spanning helices, which are coupled to G proteins.

Chemokines are released from a wide variety of cells in response to bacterial infection, viruses and agents that cause physical damage. They function mainly as chemoattractants for leukocytes, recruiting monocytes, neutrophils and other effector cells from the blood to the sites of infection or damage. They can be released by many different cell types and serve to guide cells involved in innate immunity and also the lymphocytes of the adaptive immune system. Some chemokines also have roles in the development of lymphocytes, migration and angiogenesis.

As the cytokines and chemokines are involved in a multitude of different diseases and pathogenic or deleterious conditions, there is a general need of being able to effect or modulate the expression and/or release of these compounds. Furthermore, such release/expression modulation should preferably be selective in terms of only affecting a limited number of target cytokines or chemokines.

Document [1] investigates the effect of titanium surfaces on macrophage activation and secretion of proinflammatory cytokines and chemokines. When attached to rough titanium surfaces, lipopolysaccharide (LPS) stimulated macrophages increased their secretion of the cytokines interleukin-1β (IL-1β), IL-6 and tumor necrosis factor-α (TNF-α) and the chemokines monocyte chemoattractant protein-1 (MIP-1) and macrophage inflammatory protein-1α (MCP-1α).

Document [2] discloses that titanium particles stimulate the selective induction of IL-8 and MCP-1 chemokines in human osteblast-like osteosarcoma cells.

Document [3] investigates the effect of titanium particles on cytokine release by macrophage-like cells (MLC). Titanium particles significantly enhanced MLC release of IL-1β, IL-8 and TNF-α.

Document [4] provides an overview of macrophage interactions with modified material surfaces. The document discloses that macrophages contacted with modified surfaces release of IL-1β, IL-6, IL-10 and TNF-α.

SUMMARY

The present invention overcomes these and other drawbacks of the prior art arrangements.

It is a general object of the present invention to provide a selective modulation of the chemokine 10 kDa interferon-γ inducible protein, IP-10.

It is another object of the invention to provide a composition that can be used for purifying a sample from IP-10.

Yet another object of the invention is to provide a composition that can be used for reducing IP-10 expression.

These and other objects are met by the invention as defined by the accompanying patent claims.

Briefly, the present invention involves the use of a metal or a metal oxide having the capability of selectively binding IP-10 to its surface. The metal (oxide) further has an IP-10 downregulating effect in that a contact between the metal surface and an IP-10 producing cell will cause a reduction in the IP-10 production of that cell.

The metal or metal oxide of the present invention is a metal of group 4 or 5 of the periodic table of elements. Preferred such metals include titanium, vanadium and tantalum and their oxides. More preferably, the metal is an oxide of titanium, such as titanium dioxide.

The metals and metal oxides of the present invention can be used for manufacturing a medicament for treating or preventing a disease characterized by adverse expression and/or release of IP-10. Such diseases include adverse inflammatory responses, infectious diseases, autoimmune diseases, host versus graft diseases and foreign body reactions. In all these diseases, IP-10 is a key factor in the development of the diseases and a reduction of IP-10 can be used for treating and/or preventing the diseases.

The method also involves methods of treating a disease characterized by adverse IP-10 expression and/or release in a subject. A first method involves administering a medicament of the present invention to the subject suffering from the disease. A second method involves an ex vivo treatment of a body fluid extracted from the subject. In this method, IP-10 is removed in an ex vivo filtering using the metals or metal oxides of the invention and the purified blood can then be returned to the particular subject.

SHORT DESCRIPTION OF THE DRAWINGS

The invention together with further objects and advantages thereof, may best be understood by making reference to the following description taken together with the accompanying drawings, in which:

FIG. 15 is a schematic illustration of a tool that can be used according to the present invention in scavenging IP-10 from a body fluid; and FIG. 16 is a schematic illustration of another tool that can be used according to the present invention in scavenging IP-10 from a body fluid.

DETAILED DESCRIPTION

Figure 1:
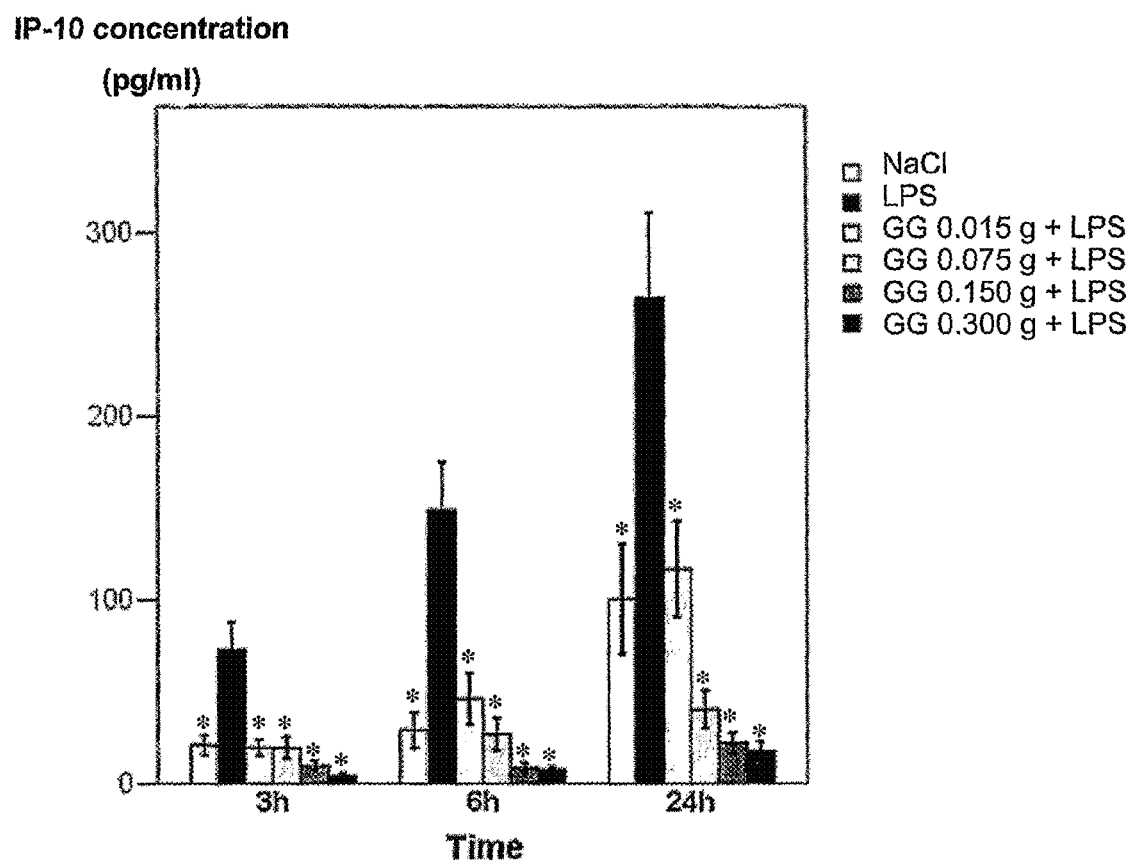
FIG. 1 is a diagram illustrating the effect of grey titanium granules (GG) on the release of IP-10 in whole human blood.

Throughout the drawings, the same reference characters will be used for corresponding or similar elements.

The present invention generally relates to a selective modulation of specific cytokines and chemokines. The present invention teaches that certain metals and metal oxides are able to reduce the expression and release of a particular chemokine and act as chemokine scavengers. This was totally unexpected, as the prior art as illustrated by documents [1-4] all show that the metal titanium causes an upregulation in the production of cytokines and chemokines by different cell types.

The present invention can therefore be used for preventing and/or treating diseased and medical conditions characterized by adverse expression or release of the particular chemokine.

The relevant chemokine that can be reduced according to the present invention is 10 kDa (10 000 Dalton) interferon-γ inducible protein, IP-10. IP-10, also denoted C—X—C motif ligand 10 (CXCL10) or Crg-2 in the art, belongs to the CDC chemokine family, which have a specific amino acid sequence of ELR (one letter amino acid code) immediately before the first cysteine. These CXC chemokines induce migration of neutrophils. However, IP-10 seems to differ from most CXC chemokines in that it has no activity on neutrophiles and targets lymphocytes specifically. IP-10 acts on the receptor CXCR3 as well as an IP-10 specific receptor on epithelia and endothelia cells [5]. IP-10 is secreted by several cell types in response to interferon-γ (IFN-γ). These cell types include monocytes, endothelial cells and fibroblasts.

The metals and oxides of metals according to the present invention that have the IP-10 reducing effect are metals and oxides of metals selected from group 4 or 5 in the periodic table of the elements. Thus, the present invention encompasses the metals titanium (Ti), zirconium (Zr), hafnium (Hf), vanadium (V), niobium (Nb) and tantalum (Ta) and different oxides of these metals. Preferred metals include titanium, tantalum and vanadium and their oxides, in particular titanium and oxides of titanium.

Titanium has three oxidation state, Ti(II), Ti(III) and Ti(IV). The present invention can use any of these oxides of titanium, i.e. Ti(II) oxide, Ti(III) oxide and Ti(IV) oxide. Ti(IV) oxide is also denoted titanium dioxide ($TiO_2$) or titania in the art. This titanium dioxide is a preferred oxide form of titanium according to the present invention. $TiO_2$ can be present in different mineral or crystalline forms, including rutile, anatase and brookite. Rutile is a tetragonal mineral usually of prismatic habit, anatase or octahedrite is a tetragonal mineral of dipyramidal habit, while brookite is an orthorhombic mineral. A preferred titanium dioxide according to the present invention is preferably in the rutile form or a mixture of the rutile and the anatase form.

A preferred oxide of zirconium is Zr(IV) oxide and Hf(IV) oxide is a preferred hafnium oxide. Vanadium is present in the oxidation states V(II), V(III), V(IV) and V(V). Available vanadium oxides include V(IV) oxide (vanadium dioxide $VO_2$) and V(V) oxide (vanadium pentoxide $V_2O_5$). Niobium oxide can be in the form of Ni(V) oxide or Ni(III) oxide and tantalum has oxidation states of Ta(II), Ta(IV) and Ta(V).

An IP-10 reducing or removing metal agent according to the present invention comprises at least one metal of group 4 or 5 and/or at least one oxide of a metal of group or 4. The metal agent could be a metal or metal oxide in substantially pure form, such as at least about 95% metal or metal oxide, preferably at least 96, 97, 98 or 99% metal or metal oxide. The metal does not necessary has to be in pure form but can be in different chemical compounds or compositions, in addition to metal oxides, with the metal. Also alloys that comprise at least one metal and/or at least one metal oxide according to the present invention can be used.

The metals and metal oxides of the present invention may reduce IP-10 according to different fundamental mechanisms.

Firstly, the metals and metal oxides act like IP-10 scavenger in that IP-10 in a surrounding medium will bind specifically to the surface of the metals and metal oxides. Thus, IP-10 will become enriched on the metal (oxide) surface and is therefore depleted from the surrounding medium. This IP-10 metal (oxide) binding is highly specific as other chemokines do not bind to the metals at the levels of IP-10, including the structurally and chemically closely related interleukin 8 (IL-8, also denoted CXCL8) that belong to the CXCL group of chemokines and monocyte chemotactic protein 1 (MCP-1, also denoted CCL2) that has a molecular size in the range of IP-10 (the two chemokines contain 98 or 99 amino acids). Blocking the metal (oxide) surface with BSA or fetal bovine serum does not affect the binding of IP-10 to the surface. The binding is also highly strong as it was not possible to remove bound IP-10 from the surface by added detergents (Tween-20).

The metal and metal oxides of the present invention act like highly specific IP-10 scavenger through the selective IP-10 metal (oxide) binding. As a consequence, the metals and metal oxides can be used for purifying a medium from unwanted IP-10 and thereby removing or at least reducing the concentration and amount of IP-10 in the medium.

Secondly, when contacting IP-10 producing cells with a metal or metal oxide of the present invention, the cell-metal interaction causes a downregulation in the IP-10 production as determined from reduced IP-10 mRNA production. This in turn has the consequence of reducing the level of newly produced IP-10. Experiments have also shown that the metals of the invention are indeed able to bind to known IP-10 producing cells, such as neutrophils and monocytes.

Thus, the metals and metal oxides of the present invention can reduce IP-10 by removing IP-10 from a medium through binding IP-10 and reducing the amount of IP-10 expression by causing a downregulation of the IP-10 mRNA production.

As the metals and metal oxides of the invention cause the IP-10 reduction at least partly by binding IP-10 molecules to its metal (oxide) surface, the metals and metal oxides are preferably in a form that has high specific surface area, i.e. surface area per weight unit.

The metal (oxide) agent can, in a first embodiment, be in the form of porous granules, grains or granulates. The granules can be produced by the well-known Hunter process or Kroll process. The resulting granules are highly porous and have a large specific surface area. This specific surface area of the porous metal granules is preferably at least 0.005 $m^2/g$, such as at least about 0.01 $m^2/g$, more preferably about or more than 0.02 $m^2/g$, such as about 0.055 $m^2/g$.

The preferred porosity of the granules implies that the granules include multiple pores, including micro and/or macro pores, which are continuous through the granules, and openings of the multiple pores and ducts or passages interconnecting at least a portion of the multiple pores. The porosity of the metal (oxide) agent is preferably at least 25%, more preferably at least 40%, such as at least about 50%. Highly porous metal granules having a porosity of about or more than 70% can be manufactured and used according to the present invention.

Instead of providing highly porous metal granules in mm or sub mm sizes, smaller metal (oxide) particles having an average diameter of 100 μm or less, such as a few μm or even smaller in the sub μm range, can be used according to the present invention. Such small metal particles or dust will provide a large surface area even at small quantities.

A first aspect of the present invention relates to the use of a metal or metal oxide in the manufacture of a medicament for treating or preventing a disease characterized by adverse expression and/or release of IP-10 in a subject. The metal is selected from at least one metal of group 4 or 5 in the periodic table of elements, at least one oxide of a metal of group 4 or 5 or a mixture of at least one group 4 or 5 metal and at least one oxide of a metal of group 4 or 5.

The metal (oxide) agent of the present invention can both be used for preventing diseases by being administered to a subject, preferably mammalian subject and more preferably a human subject, likely to suffering a disease characterized by adverse IP-10 expression. In such a case, the metal agent will cause a reduction in the production of IP-10 in the subject, by reducing the IP-10 mRNA expression. Furthermore, once/if IP-10 will be produced at high levels in the subject, the already provided metal agent will bind IP-10 to its surface, thereby reducing the level of freely circulating IP-10 and preventing IP-10 from having its deleterious effect of the disease. Thus, metal agent of the invention will function as a safeguard that can prevent the onset of an IP-10 dependent disease.

Also a patient already suffering from an IP-10 dependent disease will benefit from the medicament of the present invention as the metal agent will remove already produced IP-10 through the metal-IP-10 binding. In addition, IP-10 producing cells will be stimulated to shut down or at least reduce their IP-10 production.

The diseases or medical conditions that can be treated and/or prevented according to the present invention include IP-10 dependent diseases characterized by adverse (high) levels of IP-10 production in the subject. The present invention is in particular useful for treating or preventing adverse inflammatory reactions, where such a deleterious inflammatory reaction can have vastly different causes, such as infections, inflammatory diseases, foreign body reactions and host versus graft diseases.

When a subject becomes infected, IP-10 is normally raised as a part of the immune defense against bacteria, viruses, parasites, fungi, prions, viroids, or other pathogens. However, at situations where the normal immune system is altered, such as acquired immune deficiency syndrome (AIDS), the normal immune response can be devastating when the balance is distorted. That is, the immune system is causing more damage to the tissue/body than the infection. In AIDS patients infected with chryptospordiosis, IP-10 was significantly increased and correlated to the parasite burden. IP-10 was specifically localized to epithelial cells at the site of infection and when the infection was treated, IP-10 levels were normalized. These results suggest IP-10 to be important for the resolution of the infection in the normal immune defense, whereas in AIDS patients lacking effector cells, IP-10 may contribute to the immunopathogenesis [6].

IP-10 may promote retroviral infection, such as human immunodeficiency virus (HIV), directly [7] or through recruitment of activated target cells [8]. The level of IP-10 in the cerebrospinal fluid (CSF) is closely associated with the HIV level in the CSF which suggests that IP-10 is both a response to and a determinant of local infection [9].

The pathogenesis of the viral infection yellow fever (YF) is largely contributed by cytokines and IP-10 was found to be significantly higher in fatal YF than in nonfatal YF. These results suggest cytokine intervention to be potential therapeutic strategies for treatment of infected patients [10].

Common cold is often induced by viral infection e.g. by rhinovirus. After rhinovirus infection of human epithelial cells it has been shown that the epithelial cells produce IP-10 both in vitro and in vivo. The level of IP-10 correlated to the severity of the symptoms and therefore it is suggested that IP-10 play a role in the pathogenesis of viral induced cold [11].

Thus, the present invention can be used for treating or preventing different infectious diseases characterized by adverse IP-10 expression, in particular viral infectious diseases, including AIDS, HIV and yellow fever.

Autoimmune diseases are a particular form of inflammatory diseases, which results in an immune response against the body's own cells and tissues. IP-10 is a key player in immune responses, specifically in delayed type hypersensitivity (DTH) reactions. Such DTH reactions involve autoimmune diseases. Therefore a reduction of IP-10 caused by the metals and metal oxides of the invention can be an effective cure or preventive measure for different autoimmune diseases. Examples of autoimmune diseases that might be treated or prevented by the metal agent of the present invention include acute disseminated encephalomyelitis (ADEM), Addison's disease, ankylosing spondylitis, antiphospholipid antibody syndrome (APS), aplastic anemia, autoimmune hepatitis, autoimmune oophoritis, Coeliac disease, Crohn's disease, diabetes mellitus type 1, gestational pemphigoid, Goodpasture's syndrome, Graves' disease, Guillain-Barré syndrome (GBS), Hashimoto's disease, idiopathic thrombocytopenic purpura, Kawasaki's disease, lupus erythematosus, multiple sclerosis (MS), myasthenia gravis, opsoclonus myoclonus syndrome (OMS), optic neuritis, Ord's thyroiditis, pemphigus, pernicious anaemia, primary biliary cirrhosis, rheumatoid arthritis (RA), Reiter's syndrome, Sjögren's syndrome, Takayasu's arteritis, temporal arteritis (also known as giant cell arteritis), warm autoimmune hemolytic anemia and Wegener's granulomatosis.

MS is an autoimmune disease where the body produces antibodies against the myelin that protects nerves in the brain and spinal cord resulting in nerve loss. In patients with MS the spinal fluid contain high levels of IP-10 and accumulation of T cells in the central nervous system is very important in the pathogenesis of the disease. Therefore, IP-10 is a potential target in the search for MS therapies [12]. It has been shown that IP-10 is concentrated to the lesions of the damaged nerve tissue [13-15]. Experiments have shown that the severity of the disease state is correlated to the amount of expressed IP-10 [16], and blocking of IP-10 (antibody treatment, DNA vaccine, antisense therapy and IP-10-bound immunotoxin) resulted in clinical improvement in different mouse models [17, 18]. Usage of a metal agent according to the present invention can therefore be an effective medicament for treating or preventing MS other known IP-10 blocking agents have had positive effects.

RA is an autoimmune disease where IP-10 has been shown to be active. Up to hundred-fold increase in IP-10 concentration has been detected in synovial fluid (SF) from RA patients [19]. This IP-10 may selectively attract T-cells to the SF and contribute to the pathogenesis of RA [20]. IP-10 is induced in the SF by specific adhesion molecules and administration of antibodies against these molecules significantly inhibits IP-10 induction [21]. Data of IP-10, and other chemokines, receptor expression suggests that the chemokine system play a direct role in the destructive phase of RA [22]. A reduction in IP-10 production and IP-10 levels caused by the present invention will be beneficial in the treatment and prevention of RA.

In chronic hepatitis and autoimmune liver diseases, IP-10 is elevated and reduced after successful IFN treatment. IP-10 plays a specific role in the accumulation and death of hepatocytes in chronic hepaptitis [23]. Similar results were obtained in patients with autoimmune liver disease [24].

IP-10 is up-regulated in skin lesions from patients with chronic discoid lupus erytematosus [25] and patients with systemic lupus erythematosus (SLE) have an increased IP-10 serum level and this IP-10 level correlates to the level of disease activity [26]. Therefore, the metal (oxide) comprising medicament of the invention can be used also for treating and/or preventing these types of autoimmune diseases.

The inflammatory response to be treated or prevented by the medicament of the present invention can be due to an inflammatory disease of the gastro intestinal tract of a subject. Examples of such inflammatory diseases include inflammatory bowel disease (IBD), ulcerous colitis (UC) and Crohn's Disease (CD, which is an autoimmune disease affecting the gastro intestinal tract). These diseases are severe chronic disorders of the gastro intestinal tract with unclear origin. Increasing evidence suggest locally produced chemokines to play important roles in the progression of the diseases [27]. IBD [28], UC [29] and CD [30] are characterized by an increase in IP-10 protein expression in the inflamed bowel and the therapeutic implication by inhibiting the IP-10 signaling pathway has been discussed [31]. Blockade of IP-10 signaling by administration of antibodies against IP-10 resulted in protection from acute colitis [32] as well as chronic colitis [33]. Butyrate inhibits IP-10 release [34] and has been shown to be effective in the treatment of UC patients [35]. Mice deficient of IFN-γ, where the IP-10 pathway is abolished, are unable to develop colitis in response to dextran sulphate stimulation which normal wild type mice does [28]. Antibodies against IP-10 have been developed for the treatment of inflammatory bowel diseases [59]. These experimental results indicate that an IP-10 inhibiting medicament of the present invention can be used for treating and/or preventing inflammatory diseases of the gastro intestinal tract, including IBD, UC and CD.

The medicament of the present invention is also highly effective in treating and/or preventing inflammatory diseases. For example, IP-10 is up-regulated in skin lesions from patients with lichen (strong IP-10 expression), chronic discoid lupus erytematosus (strong IP-10 expression), allergic contact dermatitis (strong IP-10 expression), and psoriasis (weak IP-10 expression) [25]. In these lesions a high amount of infiltrating active T cells was present suggesting a functional interaction between locally produced chemokines and CXCR3-expressing T cells. Hence, the IP-10 pathway appears to play a significant role in the recruitment and maintenance of T cell infiltrates in the inflammatory skin diseases. Further adverse inflammatory responses that the present invention may treat and/or prevent include glaucoma and inflammatory responses associated with glaucoma.

IP-10 has recently been shown to be produced and secreted by adipocytes [36] and has previous been found in atherosclerotic lesions together with activated T cells [37]. Experimental studies on mice susceptible for atherosclerosis showed IP-10 to be a crucial key player in the lesion formation by local modulation of the immune system. These results in IP-10 deficient mice also showed that by inhibiting the IP-10 pathway there was a tendency to reduce the amount of pro-inflammatory T cells and increase the protective T cell population which inhibits the atherosclerotic process [38]. These latest findings in animal models suggest that blocking chemokine/chemokine receptor interactions may serve as a suitable approach to treat atherosclerosis. Likewise, chemokine antagonists that inhibit leukocyte recruitment could particularly be interesting to treat inflammation in response to myocardial infarction, the major consequence of atherosclerosis [39]. Therefore, the medicament of the present invention that results in a reduced IP-10 expression and reduced IP-10 levels in a subject can be effective for treating and/or preventing atherosclerosis.

Another adverse inflammatory response that is characterized by adverse IP-10 expression is asthma. In asthma mouse model IP-10 has been shown to contribute to the problematic hyper-reaction in the airways. IP-10 deficient mice demonstrated the opposite results compared to wild type animals which indicates IP-10 pathway to be a target of asthma therapy [40, 41]. Chemokines and IP-10 also have an impact of other conditions negatively affecting the airways of a subject. Chronic obstructive pulmonary disease (COPD) is a condition which is characterized by irreversible airway obstruction due to narrowing of small airways and destruction of the lung parenchyma. The condition causes airway inflammation, involving neutrophil granulocytes, macrophages and lymphocytes. IP-10 is upregulated in the airways of COPD patients [42]. The medicament of the present invention can therefore be used for treating and/or preventing COPD and other inflammatory conditions affecting the airways.

When transplanting an implant into a subject body, a foreign body reaction will be triggered. This reaction is a special form of adverse inflammatory reaction caused by the introduction of foreign material, e.g. implant, into the subject. Such an inflammatory reaction is characterized by an increase in IP-10 secretion, and where IP-10 may be a key effector molecule in the inflammatory reaction. Thus, a reduction in IP-10 levels will reduce the inflammatory response to the foreign implant and thereby inhibit the foreign body reaction.

The metals and metal oxides of the present invention can also be used for preventing or treating host versus graft diseases. Thus, the invention can be used in connection with graft transplantation for preventing or at least reducing the risk of graft rejection, in particular the acute phase of graft rejection. The outcome of transplantation relies in principal on the reaction in the host to the graft as rejection of the organ, tissue or cells is problematic to treat. In the acute rejection phase of a graft, IP-10 is increased and can be used as a diagnostic marker of the rejection process since IP-10 correlates to the severity of the rejection [43-46]. Experiments have shown that transplantation of grafts in the presence of antibodies directed against IP-10 or grafts from IP-10 deficient mice resulted in longer survival of the graft and fewer infiltrating T cells into the transplant [47, 48]. The reverse has also been showed, i.e. grafts survive longer in animals without ability to respond to IP-10 [49]. Antagonists to the IP-10 signaling pathway have been developed and suggested as a therapy that could improve the outcome of transplantations [50]. Taken together these results indicate that the IP-10 scavenging and reducing metal agents of the present invention can be very effective medicaments in treating or preventing graft rejection of transplanted tissue grafts, organ grafts or cell grafts, such as islets of Langerhans.

Leukocyte infiltration is involved in several cancer types (neoplasia). These infiltrating leukocytes can be potential source of growth factors for the tumor cells and angiogenic factors for endothelial cells. IP-10 has been shown to be a cytokine involved in such cancers. Furthermore, since chemokines are important mediators of leukocyte recruitment and demonstrate altered characteristics of expression and activation in chronically inflamed tissue, they have been implicated as key regulators of inflammation and angiogenesis during cancer development.

Chronic activation of innate immune cells at sites of pre-malignant tumor growth may enhance tumor development. It has also become evident that early and persistent inflammatory responses observed in or around many solid tumors, play important roles in establishing an environment suitable for neoplastic progression by providing diverse factors that alter tissue homeostasis [51-53]

The teachings of the present invention can therefore be used for treating or preventing cancer in a subject.

A second aspect of the present invention relates to a method of treating or preventing a disease or disorder characterized by adverse expression and/or release of IP-10 in a subject, preferably a mammalian subject and more preferably a human subject. The method comprises administering a metal and/or an oxide of a metal to the subject suffering from the disease, where the metal is a group 4 or 5 metal in the periodic table of the elements.

In accordance with the invention, the metals or metal oxides can be provided as pharmaceutically acceptable formulations using formulation methods known to those of ordinary skill in the art. These formulations can be administered by standard routes. In general, the copolymer may be administered intravenously, intraperitoneally, subcutaneously, buccally, rectally, dermally, nasally, orally, tracheally, bronchially, topically, by any other parenteral route or via inhalation, in the form of a pharmaceutical preparation comprising the active ingredient in a pharmaceutically acceptable dosage form. The particular administration route to use will depend, among others, on the disorder or symptom to treat and can be determined by a physician. For example, a dermal administration can be useful for treating inflammatory skin disorders, while an oral or rectal administration will be beneficial for subjects with inflammatory reactions in the gastro intestinal tract.

In intravenous administration, the pharmaceutical medical composition comprises the metal or metal oxide of the invention in a solution of a selected solvent. In a particular administration implementation, the metal or metal oxide containing solution is injected once or preferably at multiple time instants to a person in need of treatment. It could also be possible to employ a continuous or semi-continuous supply of the medicament from e.g. a medical pump or other administration equipment. Also administrations through so-called slow-release is possible and within the scope of the present invention.

In another particular implementation, a local administration in or in connection with the inflammatory site can be used to allow a relatively high local concentration of the active ingredient. This local administration can be accompanied by one or more systemic administrations.

In general, the formulations are prepared by uniformly and intimately bringing into associate the active ingredient with preferably liquid carriers or sometimes finely divided solid carriers or both, and then, if necessary, shaping the product.

Formulations suitable for parenteral administration include aqueous and non-aqueous sterile injection solutions which may contain anti-oxidants, buffers, bacteriostats and solutes which render the formulation isotonic with the blood of the intended recipient, and aqueous and non-aqueous sterile suspensions which may include suspending agents and thickening agents. The formulations may be presented in unit-dose or multi-dose containers, for example, sealed ampoules and vials, and may be stored in a freeze-dried (lyophilized) conditions requiring only the addition of the sterile liquid carrier, for example, water for injections, immediately prior to use. The aqueous phase can be physiologic phosphate buffered saline or other physiologic salt solution.

Formulations suitable for oral administration may be presented as capsules, cachets or tablets each containing a predetermined amount of the active ingredient, as a powder or granules; as a solution or a suspension or emulsion in an aqueous liquid or a non-aqueous liquid. Formulations suitable for topical administration to the skin may be presented as ointments, creams, gels and pastes comprising the ingredient to be administered in a pharmaceutical acceptable carrier. Formulations for rectal administration may be presented as a suppository with a suitable base comprising, for example, cocoa butter or a salicylate. Formulations suitable for vaginal administration may be presented as pessaries, tamports, creams, gels, pastes, foams or spray formulations containing in addition to the active ingredient such carriers as are known in the art to be appropriate.

Examples of unit dosage formulations are those containing a daily dose or unit, daily sub-dose, as herein above recited, or an appropriate fraction thereof, of the administered ingredient.

The maximum allowable dosage that can be used according to the present invention depends, among others, on the particular disorder to treat, the particular patient, the severity of an inflammatory reaction and the administration route. Experimental results have indicated that heat treated and ground titanium granules have an IP-10 binding capacity of more than 2000 pg IP-10/mg titanium particles for IP-10 spiked PBS, about 50 pg IP-10/mg titanium particles in IP-10 spiked serum and more than 3.5 pg IP-10/mg titanium particles in synovial fluid. This numbers can be used by a physician in determining the amount of metal (oxide) particles to administer as the amount of IP-10 present in a body fluid is, for several medical disorders, proportional to the severity of the disorder.

The metal agent of the invention is preferably provided (transplanted, injected or otherwise administered) in or in the neighborhood of the site in a patient where a local IP-10 expression/release control or modification is desired. This administration can be performed by transplanting the granules or particles into or close to the target site. Alternatively, especially when utilizing granulates and powder, the metal (oxide) agent of the present invention can be injected into the target site. As chemokines can be transported through the blood system of a patient, the metal agent of the present invention can also be used for a general system delivery and still being able to affect the expression and release of the selected target chemokine IP-10 from cells in the blood system and vessels, in synovial fluid, cerebrospinal fluid, ascites or in lymph fluid.

An alternative method of treating or preventing a disease characterized by adverse IP-10 expression/release involves an ex vivo treatment of a body fluid from a patient suffering from the disease. The method would involve extracting a body fluid from a subject suffering from the disease. The body fluid contains adverse high levels of IP-10 and/or IP-10 producing cells. The body fluid could be blood, blood plasma, lymph fluid, cerebrospinal fluid, ascites and/or synovial fluid, depending on the particular treatment. The extracted body fluid is contacted ex vivo with a metal or an oxide of a metal, where the metal is a group 4 or 5 metal. In this metal-fluid contact, IP-10 present in the body fluid will bind to the surface of the metal (oxide) particles and thereby be removed from the fluid. In addition, any IP-10 producing cells present in the extracted body fluid will, due to a cell-metal surface contact shut down or at least reduce their IP-10 production. The purified body fluid can then be returned to the subject. The method is similar to a traditional dialysis in that a body fluid is extracted and purified, here from IP-10, before being returned to the body.

The fluid-metal contact can generally be very short as the binding of IP-10 to the surface of the metal particles of the present invention. The contact time could be a few seconds up to some tens of minutes.

This form of treatment can be combined with other treatment arrangements, in which a body fluid is extracted from a patient and then returned to the body. For example, a traditional renal or liver dialysis can be combined with an extra purification step, in which IP-10 is removed from the body fluid, typically blood. Also patients connected to heart and/or lung machines, such as extracorporeal membrane oxygenation (ECMO) machines can benefit from an additional IP-10 purifying step according to the present invention.

This form of treatment is in particular advantageous for patients suffering from a septic shock following an infection. A crucial step in saving such a patient is that the septic shock and the inflammatory response that it causes must be combated as fast as possible. Such patients could be connected to a continuous ex vivo IP-10 dialysis according to the present invention. The level of IP-10 in the blood can then be kept at a low level until further medications succeed in removing the cause of the septic shock/infection.

The treatment method has several advantages as compared to administering the metal (oxide) agent to the subject body. Firstly, no metal (oxide) particles will be administered to the body and thereby any side effects associated with metal particle administration will not arise. Secondly, larger quantities of the metal particles and thereby a larger IP-10 scavenging capacity can be utilized as compared to direct administering to the subject body. Thirdly, the metal particles can be reused after suitable processing, in which bound IP-10 (and other molecules) have been removed from the particle surfaces.

FIGS. 15 and 16 schematically illustrate two possible arrangements or tools that can be used in connection with an ex vivo purifying of an extracted body fluid. In FIG. 15, the arrangement is basically in the form of a syringe 10 filled with metal (oxide) particles 1 of the present invention and being equipped with a filter 12 for preventing the metal particles 1 from leaving the syringe 10. During a treatment, a body fluid, such as synovial fluid, is drawn from a subject body into the syringe 1. The fluid passes the filter 12 and comes into contact with the metal particles 1. Any IP-10 molecules present in the fluid will become attached to the particle surface and are thereby removed from the fluid. Following an incubation time, the fluid can be pushed back into the body (at the same or different site as the withdrawal site). Due to careful choice of the filter pores, the particles 1 will remain in the syringe 10.

The filter pore size can be selected so that generally no cells present in the extracted body fluid will pass through filter 12 and come into contact with the metal particles 1. However, it can be advantageous if IP-10 producing cells present in the body fluid are allowed to contact with the metal particles 1 and thereby be subject to an IP-10 production reduction due to the cell-particle contact. In such a case, the filter pore size is selected to allow such IP-10 producing cells, e.g. monocytes, endothelial cells and fibroblasts, but not the metal particles 1 can pass through the filet 12.

FIG. 16 illustrates an arrangement 20 having a separate fluid input and a separate fluid output. The arrangement 20 forms a purifying chamber defined by two filters 22 and 24. This purifying chamber is filled with metal (oxide) particles 1 of the present invention. During operation, body fluid is pumped from a patient past the first filter 22. There the fluid comes into contact with the metal particles 1 and any IP-10 present in the fluid will bind the particle surface. The purified fluid can then, after incubation, be pumped past the second filter 24 and may then be returned back to the body.

It is anticipated by the present invention that the filters 12, 22, 24 employed in the arrangements of FIGS. 15 and 16 can be re-enforced by protective layers that prevent the particles 1 from damaging the filters 12, 22, 24.

The above described arrangements can also be employed for treating extracted blood that is not intended to be returned to the same subject. Thus, the arrangements can be used for reducing the IP-10 level in, for instance blood or plasma, handled by a blood bank. Such a method could then involve contacting a body sample, such as a body fluid, in vitro with a group 4 or 5 metal or an oxide of a group 4 or 5 metal to thereby scavenging IP-10 from the body sample and preferably also reduce the level of IP-10 production in the body sample.

EXPERIMENTS

Selective Cytokine and Chemokine Effect

Upon infection, the release of exogenous agents, e.g. LPS, and induction of endogenous mediators, e.g. chemokines and cytokines, contributes to the recruitment of circulating leukocytes to the inflamed tissue. Microbial products like LPS trigger multiple cell types to release cytokines, which in turn are potent inducers of chemokines. Primary cytokines act as endogenous activators of the immune response, while inducible chemokines act as secondary mediators to attract leukocytes [54]. Because of this complex interaction between cytokines and chemokines, it is important to evaluate not only the effect of metal (oxide) granules on the secretion of IP-10 but also on the release of other chemokines and cytokines, which could give an indication of synergistic interaction among them in response to LPS and treatment with titanium granules.

Incubation of Whole Human Blood Ex Vivo with Ti Granules

An ex vivo whole human blood model was used as previously described {55}. In brief, venous blood from healthy volunteers (n=7) was anticoagulated with heparin (25 U/mL blood; Leo, Ballerup, Denmark) and then incubated in microcentrifuge tubes at 37° C. with slow rotation in the presence of lipopolysaccharide (LPS) (10 ng/mL blood; LPS was derived from *Escherichia coli* serotype B6:026; Sigma, St. Louis, Mo.) and increasing dosages of grey titanium granules (0.015 g, 0.075 g, 0.150 g, 0.300 g; Hereford Metal Powder Co Ltd, UK). Blood incubated only with LPS or saline was used as a positive and negative control, respectively.

Luminex Assay

At different time points (3, 6, and 24 h), plasma was obtained by centrifugation at 7000 g for 3 min and was stored at −20° C. Plasma levels of twenty-five different cytokines, see Table 1, were analyzed using the solid phase sandwich multiplex bead immunoassays (Human cytokine 25-plex; Biosource International Inc., Camarillo, Calif., USA) according to the manufacturer's protocol. Briefly, primary antibody coated beads and incubation buffer were pipetted into 96-well filter plates. The standards and samples were incubated in the presence of the primary antibody beads for 2 h at room temperature on an orbital shaker. Following this, the wells were washed and biotinylated detection antibodies were added. After further incubation for 1 h at room temperature, the wells were washed and streptavidin-phycoerythrin solution was added to each well and incubated for 30 min at room temperature. Finally, the wells were washed thoroughly, sheath fluid was added and read using the Luminex xMAP system (Luminex Corporation, Austin, Tex., USA).

TABLE 1

| measured cytokines |
| --- |
| IL-1β |
| IL-1Ra |
| IL-2 |
| IL-2R |
| IL-4 |
| IL-5 |
| IL-6 |
| IL-7 |
| IL-8 |
| IL-10 |
| IL-12 |
| IL-13 |
| IL-15 |
| IL-17 |
| TNF-α |
| INF-α |
| INF-γ |
| GM-CSF |
| MIP-1α |
| MIP-1β |
| IP-10 |
| MIG |
| Eotaxin |
| RANTES |
| MCP-1 |

IL—interleukin
INF—interferon
IP—interferon inducible protein
MCP—monocyte chemotactic protein
MIG—monokine induced by INF-γ
MIP—macrophage inflammatory protein
TNF—tumor necrosis factor
GM-CSF—granulocyte macrophage colony stimulating factor
RANTES—regulated upon activation, normal T cell-expressed and secreted The striking result of the experiments was that the presence of the titanium granules had a profound effect by almost completely shutting down the expression of IP-10 in a dosage dependant manner.

The titanium granules had no or merely minor effects on the other cytokines whose expression were induced by LPS. Interestingly, the secretion of other chemokines from the same family (CXC chemokines) as IP-10, like IL-8, was not affected in the same way to IP-10 after treatment with titanium granules. Furthermore, chemokines having similar size as IP-10, such as MCP-1, were not affected.

The negative control (saline) and the positive control (LPS only) showed the predicted effects with normal cytokine levels in all samples incubated with saline only, and dramatically increased cytokine levels in samples incubated with LPS, mimicking the onset of an acute infectious inflammatory response. In samples incubated with titanium granules in the absence of LPS the cytokine levels were well within the range observed for the negative control, indicating that the titanium granules themselves did not elicit an inflammatory response.

Effect of Ti Granules on IP-10 Secretion in Whole Human Blood

The ex vivo whole human blood model previously described above and in [55] was used. Briefly, fresh venous blood of healthy volunteers (n=7) was added to different amounts of grey titanium granules (GG) and spiked with LPS (10 ng/ml). After 3, 6 and 24 h, plasma was isolated and analysed for IP-10 by Luminex assay. In other set of experiments, the blood was given either in pre- or post-treatment, by administering titanium granules 1 h before LPS, at the same time as LPS, or 1 h after LPS.

As shown in FIG. 1, grey titanium granules reduced the production of IP-10 in whole human blood of healthy volunteers, stimulated by LPS, in a dose-dependent manner. The results are significant in all the doses and time points tested. Mean values±SEM of 7 donors are shown, * indicates significant differences versus LPS alone (p<0.05).

In order to find out whether grey titanium granules were more effective as pre- or post-treatment, titanium granules were given 1 h prior to stimulation with LPS (−1t), at the same time as LPS (0t), or 1 h after stimulation with LPS (+1t) (n=3). Six hours after the addition of LPS, plasma was obtained and IP-10 levels were analysed by Luminex assay.

Figure 2:
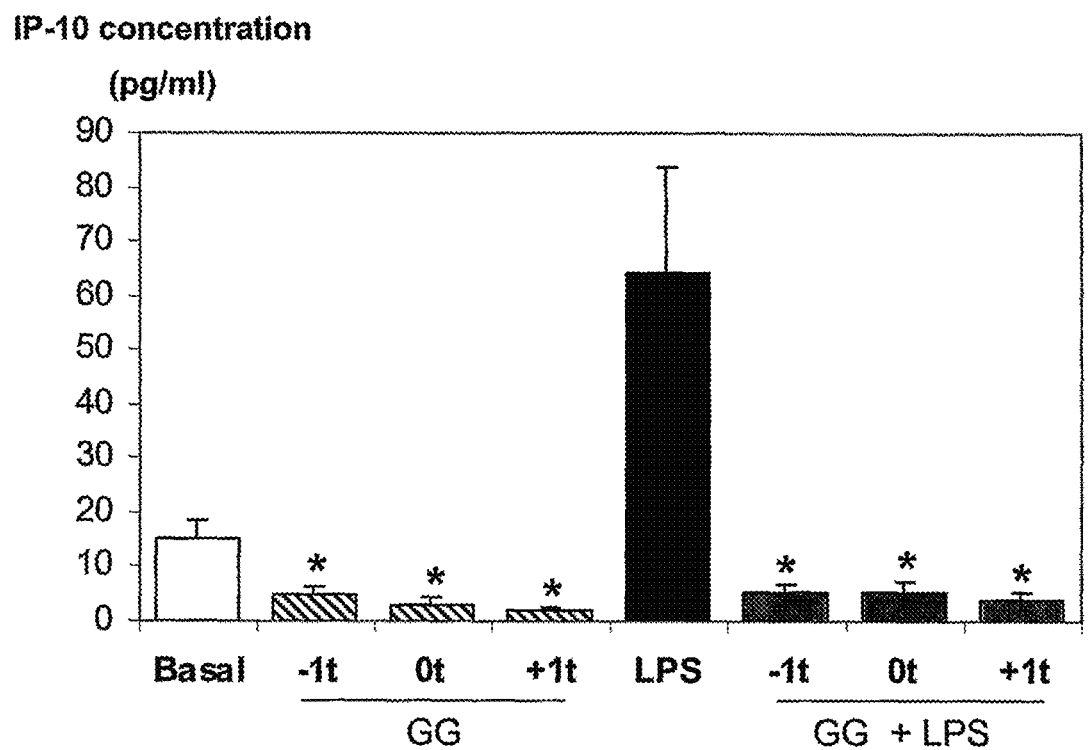
FIG. 2 is a diagram illustrating the effect of pre-treatment (−1t) versus post-treatment (+1t) with grey titanium granules (GG) on the release of IP-10 in whole human blood.

FIG. 2 shows that titanium granules were equally effective reducing IP-10 in blood that was pre-treated, or treated at the same time, and even after LPS. Basal IP-10 levels (without LPS) were as well significantly reduced in blood after the different incubation times with titanium granules (GG), to the same extent as LPS-treated samples with titanium granules (GG+LPS). Mean values±SEM of 3 donors are shown, * indicates significant differences of GG versus basal or LPS alone, respectively (p<0.05).

Effect of Ti Granules on IP-10 Gene Expression after Incubation with Human Blood The effect of Ti granules on IP-10 secretion was disclosed in the above-presented experiments. It was then investigated whether titanium granules had any effect on IP-10 gene expression.

RNA Isolation

Total RNA was isolated from total leukocytes or monocytes after incubating whole blood with titanium granules for 2 h, using RNeasy mini kit (Qiagen, Valencia, Calif., USA), according to the manufacturer's protocol. In order to isolate monocytes, a pre-processing step before the cell lysis was included to separate monocytes from whole blood, using Dynabeads CD14 coated with anti-CD14 monoclonal antibody (Invitrogen/Dynal, Carlsbad, Calif., USA). Total RNA was quantified at 260 nm using a Nanodrop spectrophotometer (NanoDrop Technologies, Wilmington, Del., USA).

Real-Time RT-PCR Analysis

Total RNA (0.5 μg) isolated from total leukocytes or monocytes was reverse transcribed to cDNA at 42° C. for 60 min using iScript cDNA Synthesis kit (BioRad, Hercules, Calif., USA) that contains both oligo(dT) and random hexamers. Each cDNA was frozen (−20° C.) in aliquots until the PCR reactions were carried out.

Real-time PCR was performed in the iCycler (BioRad, Hercules, Calif., USA) using SYBR green detection. Real-time PCR was done for three housekeeping genes: 18S ribosomal RNA (18S rRNA), glyceraldehyde-3-phosphate dehydrogenase (GAPDH) and β-actin, and four target genes: IP-10, IL-6, IL-10 and TNF-α. Table 2 lists the primers used and the parameters of the real-time PCT.

TABLE 2

Primers and PCR parameters

| Gene | Primer sequence | SEQ ID NO: | $T_m$ amplicon (° C.) | Amplicon size (bp) |
|---|---|---|---|---|
| IP-10 | S 5'-GCTACAATGAAAAAGAAGGGTGA-3' | 1 | 84.5 | 185 |
|  | A 5'-TAGGGAAGTGATGGGAGAGG-3' | 2 |  |  |
| IL-6 | S 5'-AGGAGACTTGCCTGGTGAAA-3' | 3 | 84.0 | 196 |
|  | A 5'-GCATTTGTGGTTGGGTCAG-3' | 4 |  |  |
| IL-10 | S 5'-TTATCTTGTCTCTGGGCTTGG-3' | 5 | 84.0 | 139 |
|  | A 5'-ATGAAGTGGITGGGGAATGA-3' | 6 |  |  |
| TNF-α | S 5'-CTATCTGGGAGGGGTCTTCC-3' | 7 | 88.0 | 181 |
|  | A 5'-GGGGGTAATAAAGGGATTGG-3' | 8 |  |  |
| β-Actin | S 5'-CTGGAACGGTGAAGGTGACA-3' | 9 | 85.5 | 136 |
|  | A 5'-AAGGGACTTCCTGTAACAATGCA-3' | 10 |  |  |
| 18S rRNA | S 5'-GTAACCCGTTGAACCCCATT-3' | 11 | 86.0 | 151 |
|  | A 5'-CCATCCAATCGGTAGTAGCG-3' | 12 |  |  |
| GAPDH | S 5'-TGCACCACCAACTGCTTAGC-3' | 13 | 85.0 | 87 |
|  | A 5'-GGCATGGACTGTGGTCATGAG-3' | 14 |  |  |

S Oligonucleotide sequence of sense primer
A Oligonucleotide sequence of antisense primer Each reaction contained 5 μl of cDNA, 0.5 μM of the sense and antisense specific primers, 12.5 μl of 2×IQ™ SYBR® Green Supermix (BioRad, Hercules, Calif., USA) in a final volume of 25 μl. The amplification program consisted of a preincubation step for denaturation of the template cDNA (3 min, 95° C.), followed by 40 cycles consisting of a denaturation step (15 s, 95° C.), an annealing step (15 s, 60° C.) and an extension step (30 s, 72° C.). After each cycle, fluorescence was measured at 72° C. A negative control without cDNA template was run in each assay. Samples were run in duplicate.

Real-time efficiencies were calculated from the given slopes in the iCycler software using serial dilutions, showing all the investigated transcripts high real-time PCR efficiency rates, and high linearity (r>0.99) when different concentrations were used. PCR products were subjected to a melting curve analysis on the iCycler and subsequently 2% agarose/TAE gel electrophoresis to confirm amplification specificity, Tm and amplicon size, respectively.

In order to allow relative quantification after PCR, standard curves were constructed from the standard reactions for each target and housekeeping genes by plotting Ct values (cycle threshold), i.e. the cycle number at which the fluorescence signal exceeds background, versus log cDNA dilution. The Ct readings for each of the unknown samples were then used to calculate the amount of either the target or housekeeping relative to the standard. Relative mRNA levels were calculated as the ratio of relative concentration for the target genes relative to that for the mean between the three housekeeping genes (18S rRNA, GAPDH and β-actin), to correct for RNA. Values were expressed as a percentage of negative control samples (saline), which were set to 100.

IP-10 gene expression was monitored in a) total leukocytes that remained in suspension after incubation with titanium granules, b) total leukocytes that attached to titanium granules after the incubation and c) monocytes isolated with beads coated with anti-CD14 monoclonal antibody.

Figure 3:
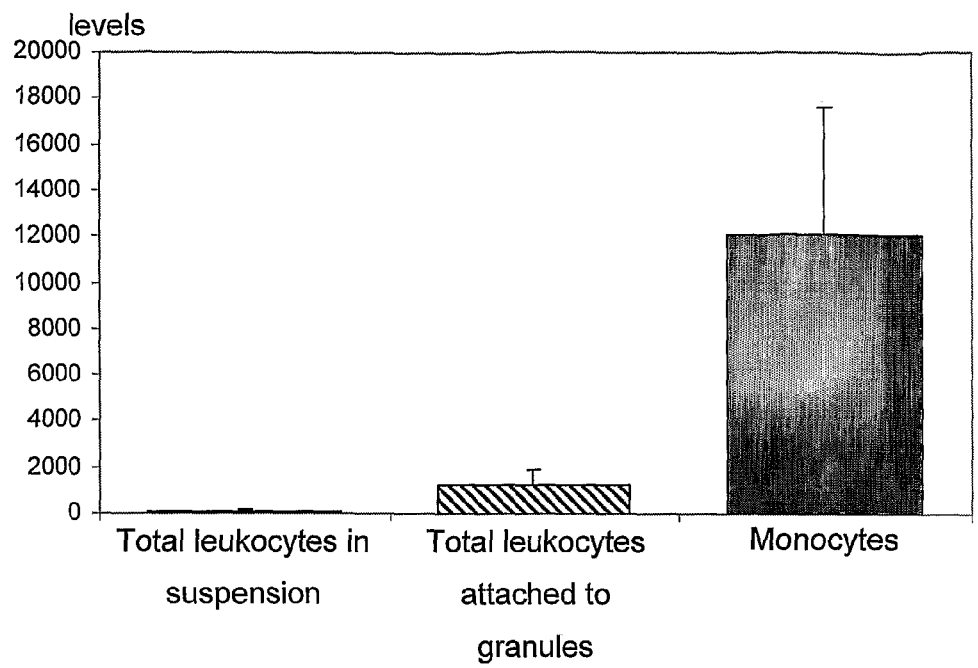
FIG. 3 is a diagram illustrating relative IP-10 gene expression in total leukocytes and monocytes after incubating whole blood with titanium granules.

FIG. 3 illustrates the relative IP-10 gene expression in total leukocytes and monocytes after incubating whole blood with titanium granules for 2 h. It is seen in FIG. 3, that the monocytes had the highest IP-10 gene expression. Leukocytes that had attached to the granules showed higher IP-10 gene expression (12-fold) than leukocytes that remained in suspension.

Figure 4:
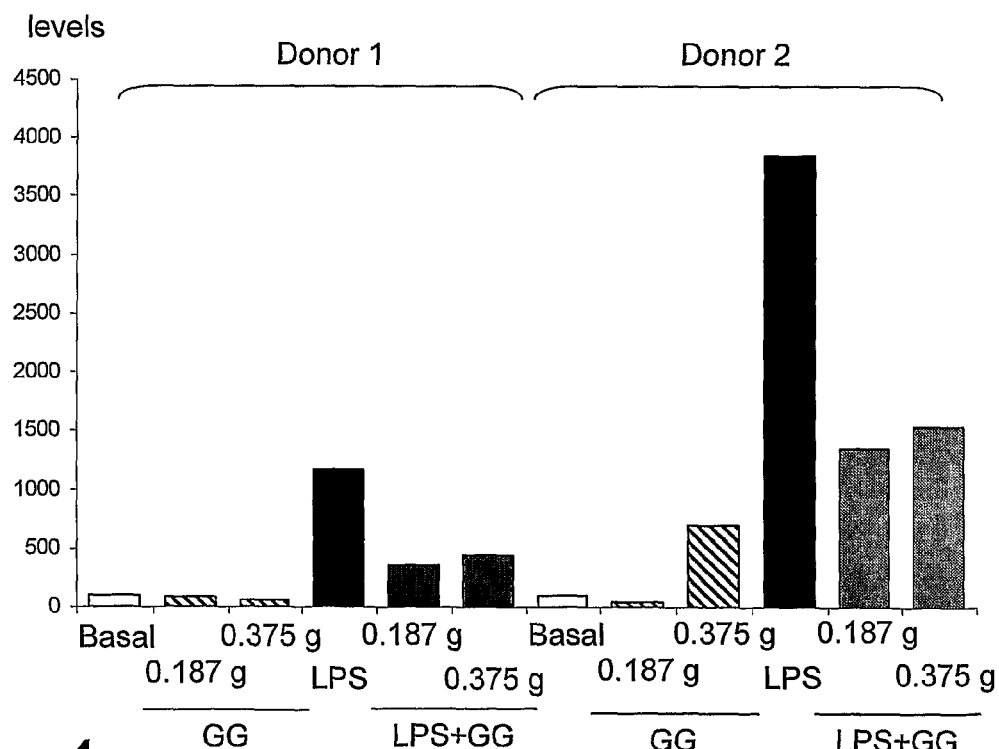
FIG. 4 is a diagram illustrating the effect of grey titanium granules (GG) on IP-10 gene expression in monocytes after incubating whole blood with titanium granules.

Human monocytes were isolated for monitoring IP-10 gene expression with titanium granules. As seen in FIG. 4, IP-10 mRNA levels were down-regulated in monocytes after incubation with titanium granules (2 h incubation) and stimulated with LPS in the two donors tested.

Total and Differential White Blood Cell Count

Experiments were conducted in order to find out which types of leukocytes that have the ability to attach to the surface of titanium granules after incubating with whole human blood.

After incubating blood with grey titanium granules for 2 h, as described above, total and differential white blood cell (WBC) counts were performed immediately in a hematology analyzer (Cell-Dyn 4000, Abbott Diagnostics Division, Santa Clara, Calif., USA).

Figure 5:
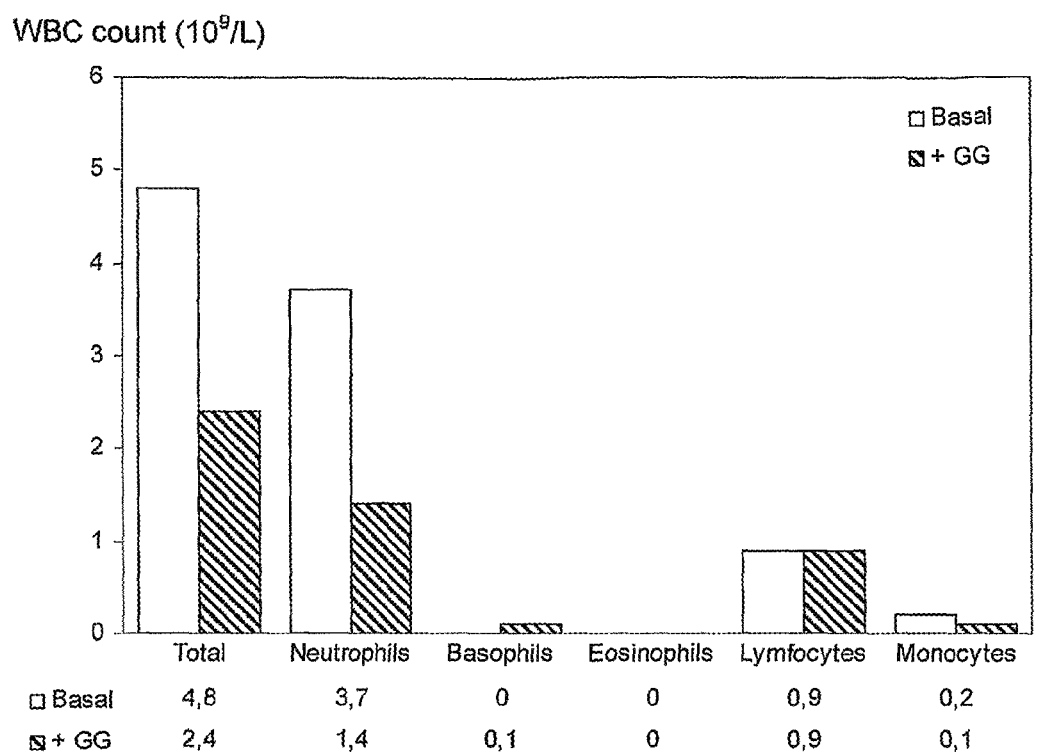
FIG. 5 is a diagram illustrating total and differential WBC count after incubation with and without grey titanium granules (GG)

FIG. 5 illustrates the total and differential WBC count (i.e. neutrophils, lymphocytes, monocytes, eosinophils and basophils, respectively) after 2 h incubation with and without grey titanium granules (GG). Titanium granules showed ability to bind neutrophils and monocytes, which are known to be IP-10 producers.

Table 3 below lists the normal range for WBC count and the differential white blood cells.

TABLE 3

Normal range of WBC count and differential WBC

|  | Number of cells per L | Percentage of total WBC |
|---|---|---|
| WBC count | 4.5-11 × $10^9$ |  |
| Polymorphonuclear neutrophils | 1.8-7.8 × $10^9$ | 50-70% |
| Band neutrophils | 0-0.7 × $10^9$ | 0-10% |
| Basophils | 0-0.2 × $10^9$ | 0-2% |
| Eosinophils | 0-045 × $10^9$ | 0-6% |
| Lymfocytes | 1-4.8 × $10^9$ | 15-45% |
| Monocytes | 0-0.8 × $10^9$ | 0-10% |

Statistics

All data are presented as mean values±SEM. Differences between groups were assessed by Student's t-test using the program SPSS® for Windows, version 14.0. Results were considered statistically significant at the P<0.05 level.

IP-10 Binding Capacity of Ti

Materials

Recombinant human IP-10 was purchased from R&D Systems and IP-10 was analyzed using sandwich ELISA technique according to the manufacturer (R&D Systems).

The effect of different titanium forms on chemokine level was studied in three different systems: a blood loop model, IP-10 spiked serum/PBS and in synovial fluid. Table 4 lists the titanium forms tested.

TABLE 4

Investigated Ti forms

| Metal | Abbreviation | Composition | Particle size | Manufacturer |
|---|---|---|---|---|
| Ti granules | GG | 99.97%, >80% sponge form | Ø~1 mm | Hereford Metal Powder Co Ltd |
| Heat treated Ti granules (900° C., 3 h) | WG | 99.97% | Ø~1 mm | Hereford Metal Powder Co Ltd |
| Sifted GG | GP | 99.97%, >80% sponge form | <0.075 mm | Hereford Metal Powder Co Ltd |
| Ground WG | WP | 99.97% | * | Hereford Metal Powder Co Ltd |

* The resulting Ti particles generally had a size in the range of sub- micrometers up to 100 μm but with an average diameter size of about 10 μm.

Blood Loop System

IP-10 was studied in a blood loop system (described previously [56, 57]), with the exception that fully heparinized (20 U/ml, Leo Pharma) blood were used. Briefly, fresh human blood from healthy volunteers was collected in surface-heparinized 60-ml syringes with a cannula (18-guage, Microlance; Becton Dickinson) that was connected to a surface-heparinized silicon tubing. During sampling, the syringe was rotated continuously. Blood (7-8 ml) was then added to each loop (PVC tube, diameter 6.3 mm, length 39 cm) leaving an air volume of ~4 ml. After the tubes were filled, the loops were closed with a heparinized stainless-steel connector and placed on a rocking device at 37° C. The loops were rocked at an amplitude setting that prevented the blood from making contact with the connectors. To initiate IP-10 production LPS from *Escherichia coli* (10 ng/ml, Sigma) was added. Titanium in different amounts and different forms were added to the loops to investigate the effect on IP-10 levels. After 10, 30, 60, 120 and 180 minutes samples were collected and plasma was stored at −20° C. until IP-10 analysis.

Spiked Serum/PBS

Serum was prepared from donated blood according to standard laboratory protocol. PBS was supplemented with 1% Bovine Serum Albumin (BSA) to prevent protein attachment to the plastic ware. Recombinant Human IP-10 was added to the serum/PBS (200-2000 pg/ml) and samples (500 μl) were incubated with different metals/oxides (20-200 mg) for 3 hours at room temperature on an orbital shaker (~400 rpm). After incubation samples were centrifuged briefly (2 minutes at 10,000 g) and supernatants were analyzed immediately for IP-10 content or stored frozen (−20° C.) until analysis.

Synovial Fluid

Synovial fluid (SF) was obtained from patients with rheumatoid arthritis at the Karolinska Hospital (Solna, Sweden) or from Oslo Rikshospital (Norway). For 3 hours 150 μl SF was incubated in room temperature on an orbital shaker (~400 rpm) with or without (10-40 mg/sample) grounded white granules (WP). When the effect of different metals/oxides was studied, 500 μl sample and 20 mg metal/oxides were used. After incubation, samples were centrifuged briefly (2 minutes at 10,000 g) and supernatants were analyzed immediately for IP-10 content or stored frozen (−20° C.) until analysis.

Figure 6:
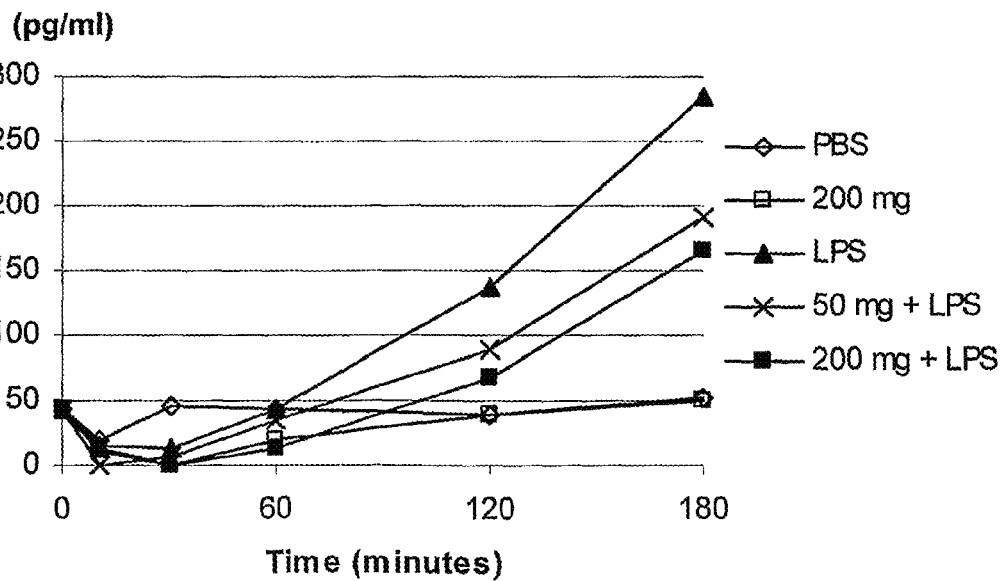
FIG. 6 is a diagram illustrating the concentration of IP-10 in a blood loop system with untreated and infected (LPS) blood with or without titanium granules.

Blood infection was simulated by LPS addition to blood loops which resulted in an increase in IP-10 production. After 2 hours the IP-10 level in the LPS treated blood was raised and further elevated after 3 hours. By adding untreated sponge titanium granules (GG) the IP-10 levels were reduced in the infected blood, see FIG. 6. There was a dose-response like reaction when different amounts of GG were added. Normal IP-10 levels were observed in uninfected blood after only GG addition. The two negative controls, PBS or PBS with 200 mg titanium granules, showed no increase in IP-10 levels.

Figure 7:
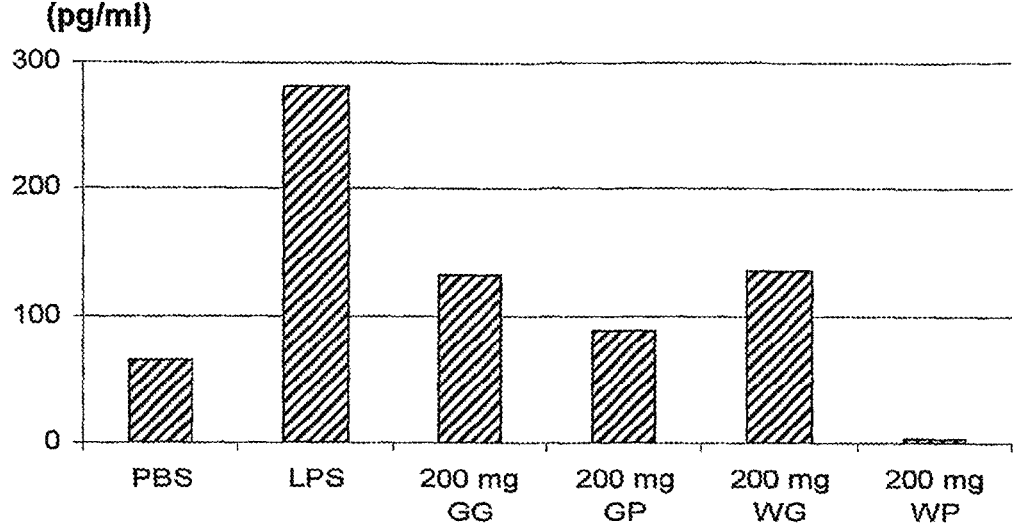
FIG. 7 is a diagram illustrating the IP-10 levels in a blood loop system with usage of grey titanium granules (GG), sifted gray titanium granules (GP), white titanium granules (WG) and ground white titanium granules (WP)

The effect of different forms of titanium granules on IP-10 levels were analyzed in the blood loop system. In whole blood both grey (GG) and white (WG) granules were found to be equally efficient in IP-10 reduction. The powder forms of the granules, GP and WP, were more efficient than whole granules and white powder (WP) had the highest IP-10 reducing capacity as is illustrated in FIG. 7. This figure illustrates the IP-10 levels in blood 180 minutes after LPS addition. The addition of 200 mg of white powder (WP) to 7 ml of infected blood resulted in a totally abolished IP-10 response. PBS treated blood was used as negative control.

Figure 8:
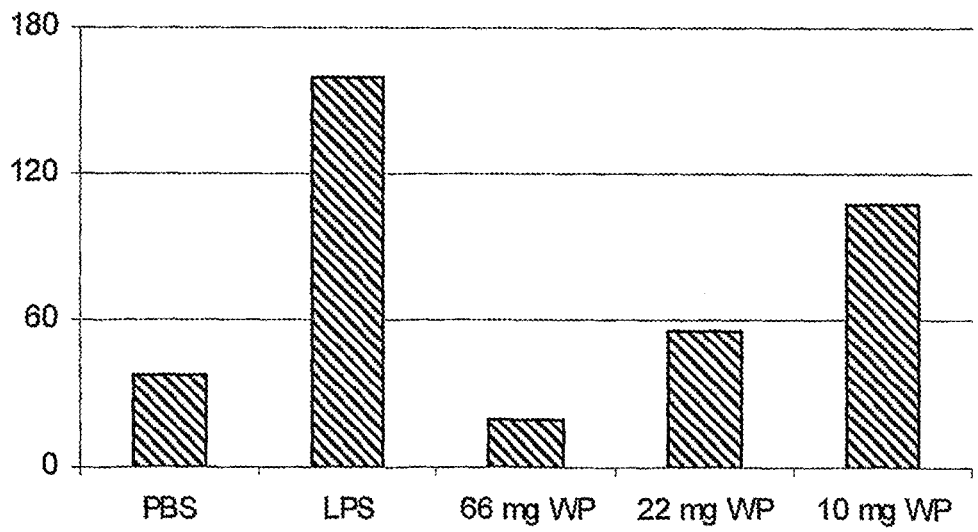
FIG. 8 is a diagram illustrating the IP-10 levels in a blood loops system using different amounts of added ground white titanium granules (WP)

In order to evaluate the IP-10 reducing capacity of grounded white titanium granules different amount of white powder (WP) were added to infected (LPS-treated) blood and the IP-10 levels were analyzed 180 minutes after the addition. IP-10 was found to be regulated in blood in a dose-response like fashion when WP was added, which is illustrated in FIG. 8. The addition of 66 mg of white powder to 7 ml of infected blood resulted in a normalized IP-10 level.

The temporal binding of IP-10 to white powder in PBS solution was studied and already after 10 minutes could WP reduce IP-10 levels to zero (3 pg IP-10/mg WP). The reduction was non-reversible and sustained for as long as studied (24 hours). It was not possible to block this binding with 5% BSA or 10% fetal bovine serum and it was not reduced after detergent addition (0.05% Tween-20).

Figure 9:
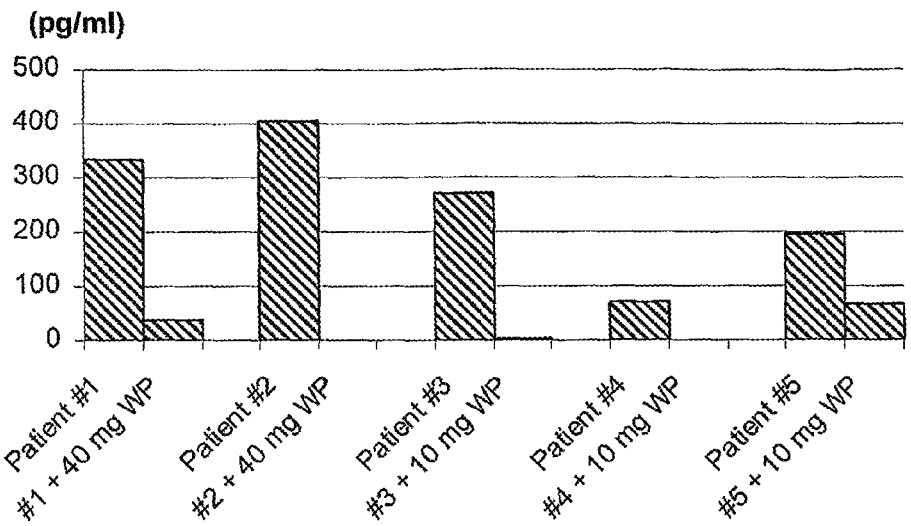
FIG. 9 is a diagram illustrating the effect of ground white titanium granules (WP) on the IP-10 level in synovial fluid from patients with rheumatoid arthritis.

The synovial fluid from inflamed joints in rheumatoid arthritis patients has previously been shown to contain high levels of IP-10, which may influence the pathogenesis of the disease [20, 58]. The IP-10 level in synovial fluid from five different patients was strongly reduced after addition of white granule powder (WP), see FIG. 9. The synovial fluid was incubated with either 10 or 40 mg of WP for 3 hours at room temperature.

Figure 10:
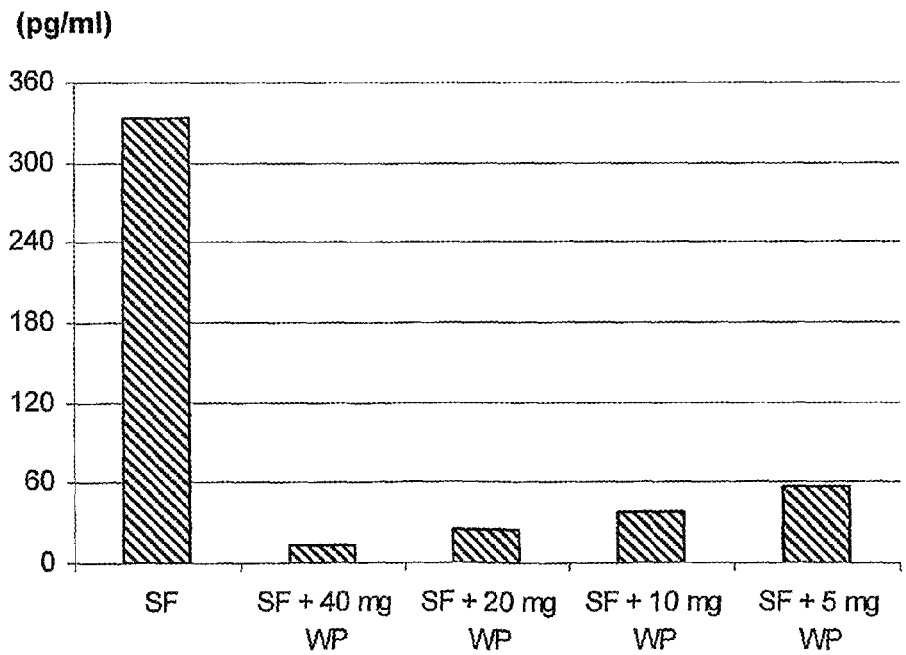
FIG. 10 is a diagram illustrating the effect of different amounts of ground white titanium granules (WP) on the IP-10 level in synovial fluid (SF) from a patient with rheumatoid arthritis.

The IP-10 binding capacity of grounded white granules in synovial fluid was studied in a system where increasing amounts of WP was added to the SF, see FIG. 10. An apparent dose-response relationship was observed in these studies.

The capacity of IP-10 reduction of grounded white granules (WP) was calculated for the different systems studied here. In spiked PBS>2000 pg IP-10/mg WP was retained, in spiked serum about 50 pg IP-10/mg WP was retained and in synovial fluid >3.5 pg IP-10/mg WP was retained.

Physical Characterization of Ti Granules
Scanning Electron Microscope

A Scanning Electron Microscope (SEM, Philips XL 30 ESEM, FEI Electron Optics, Eindhoven, Netherlands) was used to examine the surface of grey (GG) and white (WG) titanium granules.

Mercury Intrusion Porosimetry

The pore size distribution measurements of the grey (GG) and white (WG) titanium granules were performed using mercury porosimetry (Autopore IV 9500, Micromeritics, Norcross, Ga., USA). The contact angle used was 130°. The samples were evacuated for 10 min at an evacuation pressure of about 50 µmHg. The mercury filling pressure was about 0.22 psia.

Figure 11:
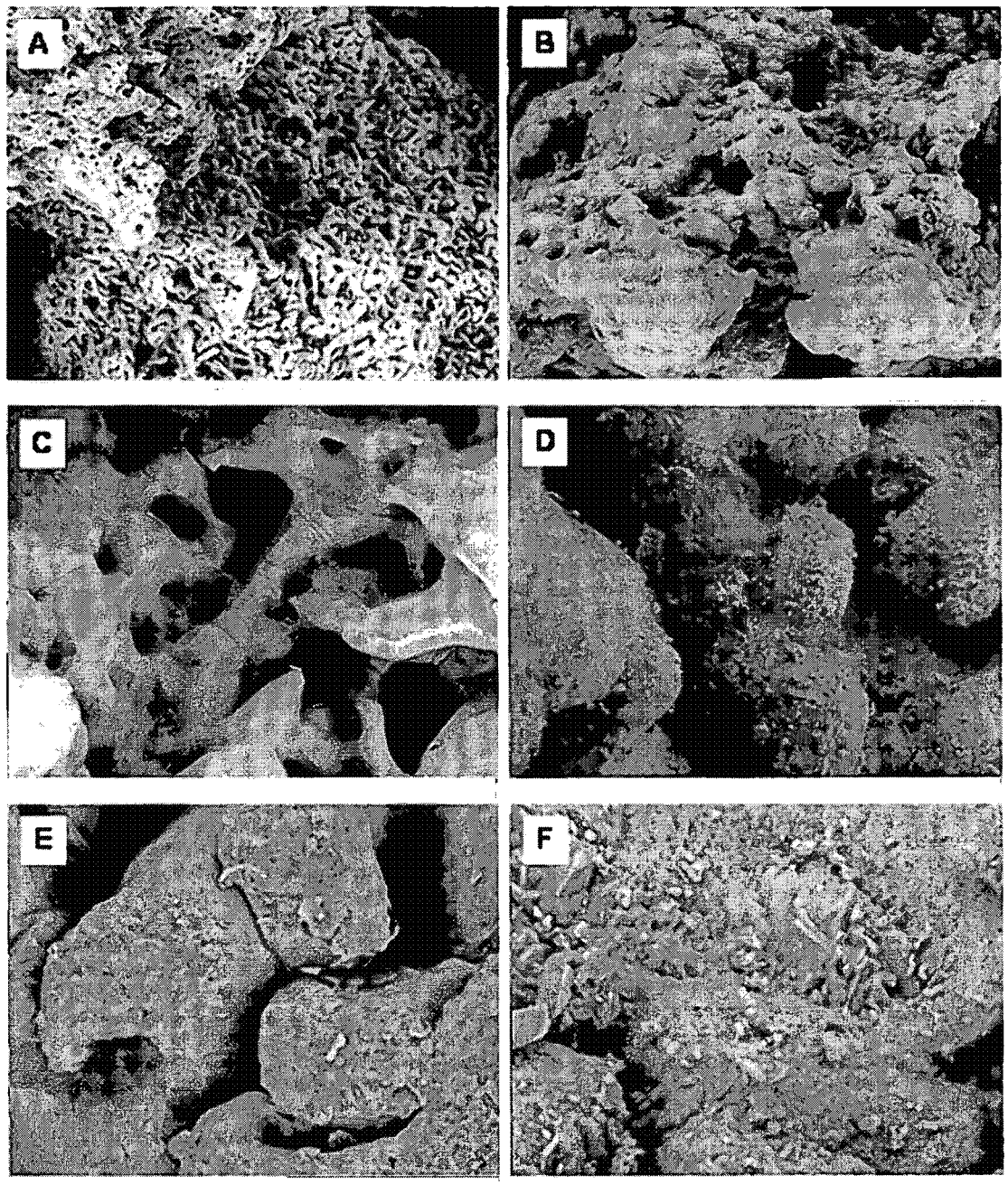
FIG. 11 illustrates scanning electronic micrographs showing grey (A, C, E) and white (B, D, F) titanium granules (250×, 2000×, 5000× magnification)

FIG. 11 shows the surface of untreated titanium granules (grey granules, GG), see A, C and E, and heat-treated (900° C., 3 h) titanium granules (white granules, WG), see B, D and E, at magnifications of 250×, 2000× and 5000×. It is seen from the micrographs that heat treatment reduced the number of pores in white granules. This is in accordance with the results obtained with the total porosity, which was 73% and 57% for grey and white titanium granules, respectively. The total intrusion volume, total surface area, median pore diameter, bulk density, apparent density and percent porosity for grey and white titanium granules are given in Table 5.

TABLE 5 intrusion data summary for grey and white Ti granules

| Property | Grey Ti granules | White Ti granules |
|---|---|---|
| Total intrusion volume (mL/g) | 0.7394 | 0.4895 |
| Total surface area (m$^2$/g) | 0.055 | 0.021 |
| Median pore diameter (Volume) (µm) | 180.0 | 328.7 |
| Median pore diameter (Area) (µm) | 21.0 | 28.9 |
| Average pore diameter (4 V/A) (µm) | 53.7 | 93.3 |
| Bulk density at 0.22 psia (g/mL) | 0.9913 | 1.1614 |
| Apparent (skeletal) density (g/mL) | 3.7126 | 2.6916 |
| Porosity (%) | 73.3 | 56.9 |

Figure 12:
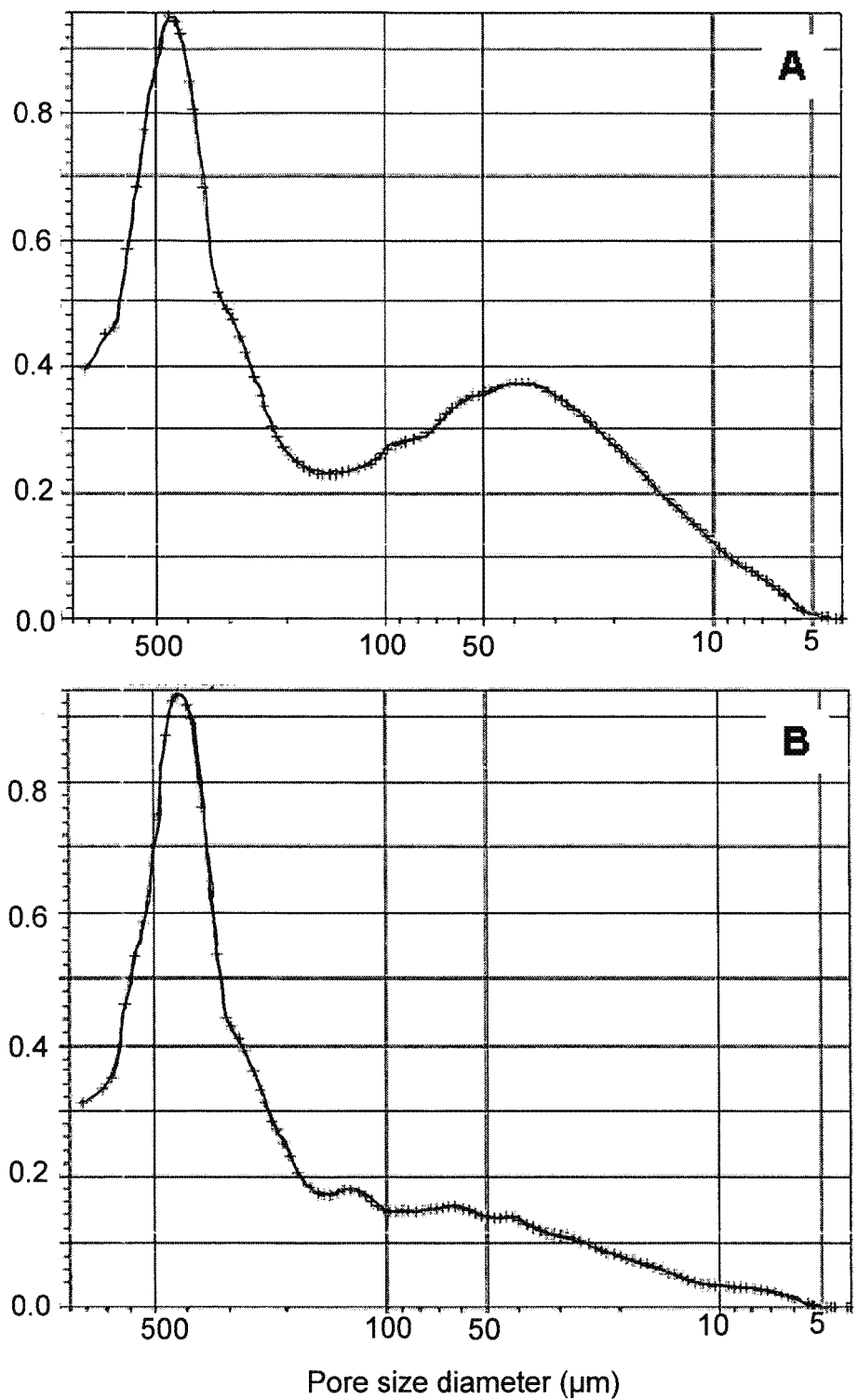
FIG. 12 illustrates log differential mercury intrusion volume to pore size curves for grey (A) and white (B) titanium granules.

FIG. 12 illustrates log differential mercury intrusion volume to pore size for grey (A) and white (B) Ti granules. As shown in the figure, micropores (~40 µm) present in grey granules were absent in white granules, while macropores (~400 µm) were not affected by the heat treatment.

IP-10 Binding Capacity of Ti and Other Metals
Materials

In order to investigate the IP-10 binding capacity of different titanium oxides and other metals, two different systems: IP-10 spiked serum and in synovial fluid were used. Table 6 lists the other metals and oxides that were studies in addition to the titanium forms listed in Table 6.

TABLE 6

Investigated metals

| Metal | Abbreviation | Composition | Particle size | Manufacturer |
|---|---|---|---|---|
| TiO$_2$ (80% Anatase/20% Rutile) | TiO$_2$(80A/20R) | 99.5% | ~21 nm | Degussa |
| Ti(IV) oxide (Rutile) | Ti(IV)Ox(R) | 99.9% | <5 µm | Aldrich |
| TiO$_2$ (Anatase) | TiO$_2$(A) | — | — | Sachtleben |
| Titaniumcarbide | TiCarb | — | <2 µm | Roth |
| Ti(II) oxide | Ti(II)Ox | 99.9% | <45 µm | Aldrich |
| Ti powder | Ti ~325 | 99.9% | <45 µm | Aldrich |
| Ta powder | Ta ~325 | 99.9% | <45 µm | Aldrich |
| V powder | V ~325 | 99.5% | <45 µm | Aldrich |
| Mn(II, III) oxide | Mn(II, III)Ox | 97% | — | Aldrich |
| Ni(II) oxide | Ni(II)Ox | 76-77% | <10 µm | Aldrich |
| Cu(II) oxide | Cu(II)Ox | 97% | <5 µm | Aldrich |
| Fe(III) oxide | Fe(III)Ox | 98% | <5 µm | Aldrich |
| Zn oxide | ZnOx | 99% | — | Fluka |

Figure 13:
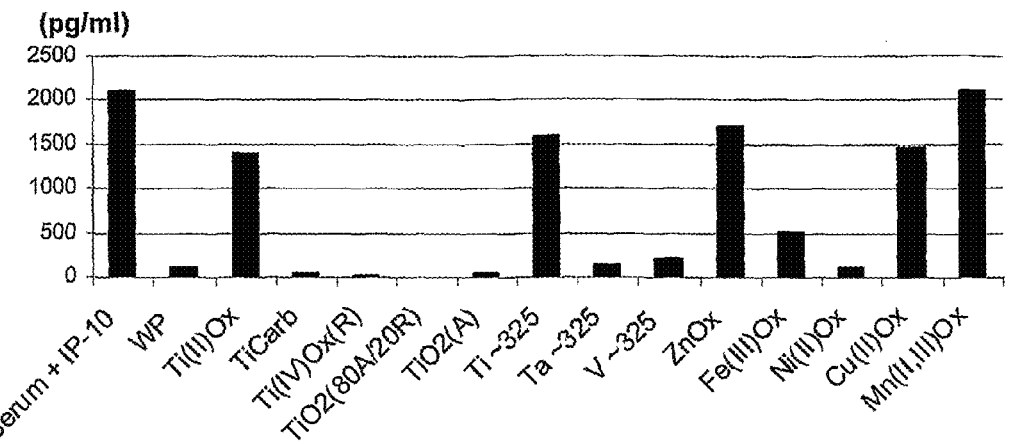
FIG. 13 is a diagram illustrating the effect of different titanium forms and other metals on IP-10 in serum spiked with IP-10.

20 mg of the different metals were added to serum spiked (200 pg/ml) with IP-10. FIG. 13 shows the results from these experiments. Among the different titanium forms it can be concluded that white titanium (WP, Ti(IV)Ox(R), TiO$_2$(80A/20R), TiO$_2$(A)) is the most efficient form to lower IP-10 levels in blood. Both tantalum and vanadium, which are closely related to titanium, were efficient in IP-10 lowering. Neither zinc, copper nor manganese was affecting IP-10 levels in spiked serum to any extent.

Figure 14:
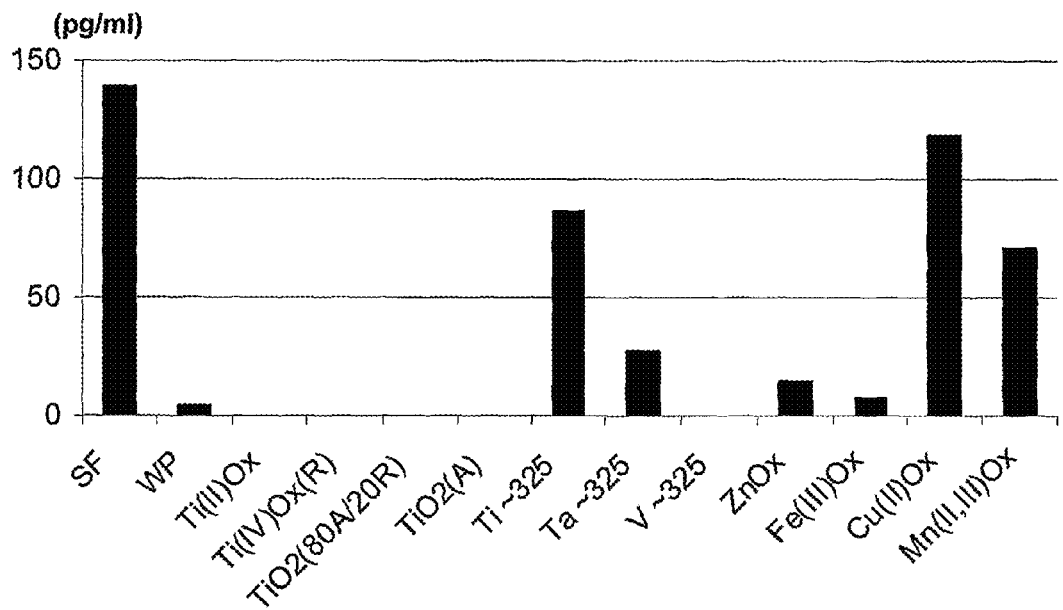
FIG. 14 is a diagram illustrating the effect of different titanium forms and other metals on IP-10 in synovial fluid (SF)

The effect of these different oxides and metals on IP-10 levels was also investigated in synovial fluid, see FIG. 14. These results did in general confirm the results from IP-10 spiked serum with some exceptions. In SF Ti(II)oxid (black) and zinc were more efficient than observed in studies on serum, whereas the other metals affected the IP-10 levels to the same extent.

It will be understood by a person skilled in the art that various modifications and changes may be made to the present invention without departure from the scope thereof, which is defined by the appended claims.

REFERENCES

[1] Refai et al., "Effect of titanium surface topography on macrophage activation and secretion of proinflammatory cytokines and chemokines", *Journal of Biomedical Materials Research Part A*, 2004, 70(2): 194-205

[2] Fritz et al., "Chemokine gene activation in human bone marrow-derived osteoblasts following exposure to particulate wear debris", *Journal of Biomedical Materials Research Part A*, 2006, 77(1): 192-201

[3] Rader et al., "Cytokine response of human macrophage-like cells after contact with polyethylene and pure titanium particles", *The Journal of Arthroplasty*, 1999, 14(7): 840-848

[4] Thomsen and Gretzer, "Macrophage interactions with modified material surfaces", *Current Opinion in Solid State and Materials Science*, 2001, 5: 163-176

[5] Soejima and Rollins, "A functional IFN-gamma-inducible protein-10/CXCL10-specific receptor expressed by epithelial and endothelial cells that is neither CXCR3 nor glycosaminoglycan", *The Journal of Immunology*, 2001, 167(11): 6576-6582

[6] Wang et al., "High levels of CXCL10 are produced by intestinal epithelial cells in AIDS patients with active cryptosporidiosis but not after reconstitution of immunity", *Infection and Immunity*, 2007, 75(1): 481-487

[7] Lane et al., "The C—X—C chemokine IP-10 stimulates HIV-1 replication", *Virology*, 2003, 307(1): 122-134

[8] Reinhart, "Chemokine induction by HIV-1: recruitment to the cause", *Trends in Immunology*, 2003, 24(7): 351-353

[9] Cinque et al., "Cerebrospinal fluid interferon-gamma-inducible protein 10 (IP-10, CXCL10) in HIV-1 infection", *Journal of Neuroimmunology*, 2005, 168(1-2): 154-163

[10] ter Meulen et al., "Activation of the cytokine network and unfavorable outcome in patients with yellow fever", *The Journal of Infectious Diseases*, 2004, 190(10): 1821-1827

[11] Spurrell et al., "Human airway epithelial cells produce IP-10 (CXCL10) in vitro and in vivo upon rhinovirus infection", *American Journal of Physiology: Lung Cellular and Molecular Physiology*, 2005, 289(1): L85-95

[12] Sorensen, "Targeting the chemokine receptor CXCR3 and its ligand CXCL10 in the central nervous system: potential therapy for inflammatory demyelinating disease?", *Current Neurovascular Research*, 2004, 1(2): 183-190

[13] Simpson et al., "Expression of the interferon-gamma-inducible chemokines IP-10 and Mig and their receptor, CXCR3, in multiple sclerosis lesions", *Neuropathology and Applied Neurobiology*, 2000, 26(2): 133-142

[14] Sorensen et al., "Multiple sclerosis: a study of CXCL10 and CXCR3 co-localization in the inflamed central nervous system", *Journal of Neuroimmunoly*, 2002, 127(1-2): 59-68

[15] Tanuma et al., "Chemokine expression by astrocytes plays a role in microglia/macrophage activation and subsequent neurodegeneration in secondary progressive multiple sclerosis", *Acta Neuropathologica* (Berlin), 2006, 112(2): 195-204

[16] Mahad et al., "Expression of chemokines in the CSF and correlation with clinical disease activity in patients with multiple sclerosis", *Journal of Neurology, Neurosurgery and Psychiatry*, 2002, 72(4): 498-502

[17] Tsunoda et al., Distinct roles for IP-10/CXCL10 in three animal models, Theiler's virus infection, EAE, and MHV infection, for multiple sclerosis: implication of differing roles for IP-10", *Multiple Sclerosis*, 2004, 10(1): 26-34

[18] Chen et al., "In vivo administration of plasmid DNA encoding recombinant immunotoxin DT390-IP-10 attenuates experimental autoimmune encephalomyelitis", *Journal of Autoimmunity*, 2007, 28(1): 30-40

[19] Patel et al., "CXCR3 and CCR5 ligands in rheumatoid arthritis synovium", *Clinical Immunology*, 2001, 98(1): 39-45

[20] Aggarwal et al., "Chemokine and chemokine receptor analysis reveals elevated interferon-inducible protein-10 (IP)-10/CXCL10 levels and increased number of CCR5+ and CXCR3+ CD4 T cells in synovial fluid of patients with enthesitis-related arthritis (ERA)", *Clinical and Experimental Immunology* 2007, 148(3): 515-519

[21] Hanaoka et al., "A novel mechanism for the regulation of IFN-gamma inducible protein-10 expression in rheumatoid arthritis", *Arthritis Research & Therapy*, 2003, 5(2): R74-81

[22] Garcia-Vicuna et al., "CC and CXC chemokine receptors mediate migration, proliferation, and matrix metalloproteinase production by fibroblast-like synoviocytes from rheumatoid arthritis patients", *Arthritis & Rheumatism*, 2004, 50(12): 3866-3877

[23] Narumi et al., Expression of IFN-inducible protein-10 in chronic hepatitis", *The Journal of Immunology*, 1997, 158(11): 5536-5544

[24] Nishioji et al., "Increase of chemokine interferon-inducible protein-10 (IP-10) in the serum of patients with autoimmune liver diseases and increase of its mRNA expression in hepatocytes", *Clinical and Experimental Immunology* 2001, 123(2): 271-279

[25] Flier et al., "Differential expression of CXCR3 targeting chemokines CXCL10, CXCL9, and CXCL11 in different types of skin inflammation", *The Journal of Pathology*, 2001, 194(4): 398-405

[26] Narumi et al., "Serum levels of IFN-inducible protein-10 relating to the activity of systemic lupus erythematosus", *Cytokine*, 2000, 12(10): 1561-1565

[27] Danese and Gasbarrini, "Chemokines in inflammatory bowel disease", *Journal of Clinical Pathology*, 2005, 58(10): 1025-1027

[28] Ito et al., "Interferon-gamma is causatively involved in experimental inflammatory bowel disease in mice", *Clinical and Experimental Immunology*, 2006, 146(2): 330-338

[29] Uguccioni et al., "Increased expression of IP-10, IL-8, MCP-1, and MCP-3 in ulcerative colitis", *The American Journal of Pathology*, 1999, 155(2): 331-336

[30] Singh et al., "IFN-gamma-inducible chemokines enhance adaptive immunity and colitis" *Journal of Interferon and Cytokine Research*, 2003, 23(10): 591-600

[31] Singh et al., "CXCR3 axis: role in inflammatory bowel disease and its therapeutic implication", *Endocrine, Metabolic & Immune Disorders—Drug Targets*, 2007, 7(2): 111-123

[32] Sasaki et al., "Blockade of CXCL10 protects mice from acute colitis and enhances crypt cell survival", *European Journal of Immunology*, 2002, 32(11): 3197-3205

[33] Suzuki et al., "Blockade of interferon-gamma-inducible protein-10 attenuates chronic experimental colitis by blocking cellular trafficking and protecting intestinal epithelial cells", *Pathology International*, 2007, 57(7): 413-420

[34] Inatomi et al., "Butyrate blocks interferon-gamma-inducible protein-10 release in human intestinal subepithelial myofibroblasts", *Journal of Gastroenterology*, 2005, 40(5): 483-489

[35] Breuer et al., "Rectal irrigation with short-chain fatty acids for distal ulcerative colitis. Preliminary report," *Digestive Diseases and Science*, 1991, 36(2): 185-187

[36] Herder et al., "Constitutive and regulated expression and secretion of interferon-gamma-inducible protein 10 (IP-10/CXCL10) in human adipocytes", *International Journal of Obesity (Loud)*, 2007, 31(3): 403-410

[37] Mach et al., "Differential expression of three T lymphocyte-activating CXC chemokines by human atheroma-associated cells", *The Journal of Clinical Investigation*, 199, 104(8): 1041-1050

[38] Heller et al., "Chemokine CXCL10 promotes atherogenesis by modulating the local balance of effector and regulatory T cells", *Circulation*, 2006, 113(19): 2301-2312

[39] Braunersreuther et al., "The specific role of chemokines in atherosclerosis", *Thrombosis and Haemostasis*, 2007, 97(5): 714-721

[40] Bisset and Schmid-Grendelmeier, "Chemokines and their receptors in the pathogenesis of allergic asthma: progress and perspective," *Current Opinion in Pulmonary Medicine*, 2005, 11(1): 35-42

[41] Medoff et al., "IFN-gamma-inducible protein 10 (CXCL10) contributes to airway hyperreactivity and airway inflammation in a mouse model of asthma", *The Journal of Immunology*, 2002, 168(10): 5278-5286

[42] Larsson, "Aspects on pathophysiological mechanism in COPD", *Journal of Internal Medicine*, 2007, 262: 311-340

[43] Hu et al., "Elevation of CXCR3-binding chemokines in urine indicates acute renal-allograft dysfunction", *American Journal of Transplantation*, 2004, 4(3): 432-437

[44] Kanmaz et al., "Surveillance of acute rejection in baboon renal transplantation by elevation of interferon-gamma inducible protein-10 and monokine induced by interferon-gamma in urine", *Transplantation*, 2004, 78(7): 1002-1007

[45] Zhu et al., "Changes of inducible protein-10 and regulated upon activation, normal T cell expressed and secreted protein in acute rejection of pancreas transplantation in rats", *World Journal of Gastroenterology*, 2006, 12 (26): 4156-4160

[46] Melter et al., "Expression of the chemokine receptor CXCR3 and its ligand IP-10 during human cardiac allograft rejection", *Circulation*, 2001, 104(21): 2558-2564

[47] Baker et al., "Genetic deletion of chemokine receptor CXCR3 or antibody blockade of its ligand IP-10 modulates posttransplantation graft-site lymphocytic infiltrates and prolongs functional graft survival in pancreatic islet allograft recipients", *Surgery*, 2003 134(2): 126-133

[48] Hancock et al., "Donor-derived IP-10 initiates development of acute allograft rejection", *The Journal of Experimental Medicine*, 2001, 193(8): 975-980

[49] Hancock et al., "Requirement of the chemokine receptor CXCR3 for acute allograft rejection", *The Journal of Experimental Medicine*, 2000, 192(10): 1515-1520

[50] Ondeykal et al., "Discovery of structurally diverse natural product antagonists of chemokine receptor CXCR3", *Molecular Diversity*, 2005, 9(1-3): 123-129

[51] Coussens and Werb, "Inflammation and cancer", *Nature*, 2002, 420(6917): 860-867

[52] van Kempen et al., "The tumor microenvironment: a critical determinant of neoplastic evolution", *European Journal of Cell Biology*, 2003, 82(11): 539-548

[53] Robinson et al., "Soluble mediators of inflammation during tumor development", *Advances in Cancer Research*, 2005, 93: 159-187

[54] Gouwym et al., "Synergy in cytokine and chemokine networks amplifies the inflammatory response", *Cytokine & Growth Factor Reviews*, 2005, 16(6): 561-580

[55] Wang et al., "Cytokine modulation in experimental endotoxemia: characterization of an ex vivo whole blood model", *European Surgical Research*, 2000, 32(2): 65-73

[56] Bennet et al., "Incompatibility between human blood and isolated islets of Langerhans: a finding with implications for clinical intraportal islet transplantation?", *Diabetes*, 1999, 48(10): 1907-1914

[57] Gong et al., "Tubing loops as a model for cardiopulmonary bypass circuits: both the biomaterial and the blood-gas phase interface induce complement activation in an in vitro model", *Journal of Clinical Immunology*, 1996, 16(4): 222-229

[58] Patel et al., "CXCR3 and CCR5 ligans in rheumatoid arthritis synovium", *Clinical Immunology*, 2001, 98(1): 39-45

[59] WO 2005/060457

The invention claimed is:

1. A body fluid purifying arrangement comprising:
   a purifying chamber having a fluid input and a fluid output;
   a first filter arranged in connection said fluid input;
   a second filter arranged in connection with said fluid output; and
   granules or particles made of a metal or an oxide of a metal retained within said purifying chamber by said first filter and said second filter to purify a body fluid passing through said purifying chamber from 10 kDa interferon-γ inducible protein, IP-10, wherein said metal is a metal of group 4 or 5 of the periodic table of the elements and selected from the group consisting of titanium, zirconium, hafnium, niobium and tantalum.

2. The body fluid purifying arrangement according to claim 1, wherein said metal is selected from a group of titanium and tantalum.

3. The body fluid purifying arrangement according to claim 1, wherein said oxide of said metal is selected from a group consisting of an oxide of titanium and an oxide of tantalum.

4. The body fluid purifying arrangement according to claim 3, wherein said oxide of titanium is a titanium dioxide.

5. The body fluid purifying arrangement according to claim 4, wherein said titanium dioxide is a titanium dioxide of rutile form or a mixture of the rutile and anatase forms.

6. The body fluid purifying arrangement according to claim 1, wherein said metal or said oxide of said metal is in the form of granules or particles having a total porosity of at least about 50%.

7. The body fluid purifying arrangement according to claim 1, wherein said metal or said oxide of said metal is in the form of granules or particles having a total surface area of at least about 0.01 $m^2/g$.

8. The body fluid purifying arrangement according to claim 1, wherein said metal or said oxide of said metal is in the form of particles having an average particle diameter below 100 μm.

9. The body fluid purifying arrangement according to claim 1, wherein body fluid is selected from a group consisting of blood, blood plasma, lymph fluid, cerebrospinal fluid, ascites and synovial fluid.

10. A method of reducing 10 kDa interferon-γ inducible protein, IP-10, in a body fluid, said method comprising:

pumping said body fluid past a first filter arranged in connection with a fluid input of a purifying chamber comprised in a body fluid purifying arrangement according to claim 1 and into said purifying chamber to contact said body fluid with granules or particles made of a metal or an oxide of a metal retained within said purifying chamber by said first filter and a second filter arranged in connection with a fluid output of said purifying chamber to purify said body fluid from IP-10; and pumping said body fluid purified from IP-10 out from said purifying chamber and past said second filter, wherein said metal is a metal of group 4 or 5 of the periodic table of the elements and selected from the group consisting of titanium, zirconium, hafnium, niobium and tantalum.

11. A body fluid purifying arrangement in the form of a syringe comprising:

a purifying chamber having a common fluid input and fluid output;

a filter arranged in connection with said common fluid input and output; and granules or particles made of a metal or an oxide of a metal retained within said purifying chamber by said filter to purify a body fluid passing through said purifying chamber from 10 kDa interferon-γ inducible protein, IP-10, wherein said metal is a metal of group 4 or 5 of the periodic table of the elements and selected from the group consisting of titanium, zirconium, hafnium, niobium and tantalum.

12. The body fluid purifying arrangement according to claim 11, wherein said metal is selected from a group of titanium and tantalum.

13. The body fluid purifying arrangement according to claim 11, wherein said oxide of said metal is selected from a group consisting of an oxide of titanium and an oxide of tantalum.

14. The body fluid purifying arrangement according to claim 13, wherein said oxide of titanium is a titanium dioxide.

15. The body fluid purifying arrangement according to claim 14, wherein said titanium dioxide is a titanium dioxide of rutile form or a mixture of the rutile and anatase forms.

16. The body fluid purifying arrangement according to claim 11, wherein said metal or said oxide of said metal is in the form of granules or particles having a total porosity of at least about 50%.

17. The body fluid purifying arrangement according to claim 11, wherein said metal or said oxide of said metal is in the form of granules or particles having a total surface area of at least about 0.01 $m^2/g$.

18. The body fluid purifying arrangement according to claim 11, wherein said metal or said oxide of said metal is in the form of particles having an average particle diameter below 100 μm.

19. The body fluid purifying arrangement according to claim 11, wherein body fluid is selected from a group consisting of blood, blood plasma, lymph fluid, cerebrospinal fluid, ascites and synovial fluid.

20. A method of reducing 10 kDa interferon-γ inducible protein, IP-10, in a body fluid, said method comprising:

drawing a body fluid past a filter arranged in connection with a common fluid input and output of a purifying chamber comprised in a body fluid purifying arrangement according to claim 11 and into said purifying chamber to contact said body fluid with granules or particles made of a metal or an oxide of a metal retained within said purifying chamber by said filter to purify said body fluid from IP-10; and pushing said body fluid purified from IP-10 out form said purifying chamber and past said filter wherein said metal is a metal of group 4 or 5 of the periodic table of the elements and selected from the group consisting of titanium, zirconium, hafnium, niobium and tantalum.

* * * * *